(12) United States Patent
Kuwajima et al.

(10) Patent No.: US 7,451,637 B2
(45) Date of Patent: Nov. 18, 2008

(54) METHOD OF EVALUATING CONTACT CHARACTERISTICS, AND COMPUTER PRODUCT

(75) Inventors: Masatoshi Kuwajima, Kanagawa (JP); Toshihiko Okano, Kanagawa (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 529 days.

(21) Appl. No.: 11/172,926

(22) Filed: Jul. 5, 2005

(65) Prior Publication Data
US 2006/0005613 A1  Jan. 12, 2006

(30) Foreign Application Priority Data
Jul. 6, 2004  (JP) .............................. 2004-198967

(51) Int. Cl.
*G01B 5/28* (2006.01)
(52) U.S. Cl. .......................................... 73/105; 73/104
(58) Field of Classification Search ................... 73/104, 73/105
See application file for complete search history.

(56) References Cited

U.S. PATENT DOCUMENTS

| | | | | |
|---|---|---|---|---|
| 4,484,475 A * | 11/1984 | Ogura et al. ................... | 73/579 |
| 5,740,616 A * | 4/1998 | Seddon et al. ................. | 33/554 |
| 6,435,014 B1 * | 8/2002 | Palmquist et al. ............. | 73/104 |
| 6,886,394 B1 * | 5/2005 | Kume ........................... | 73/105 |
| 7,024,921 B2 * | 4/2006 | Sutton .......................... | 73/54.04 |
| 7,308,822 B2 * | 12/2007 | Sutton .......................... | 73/104 |
| 7,325,445 B1 * | 2/2008 | Bowman ....................... | 73/104 |
| 7,347,084 B2 * | 3/2008 | Tolzer et al. .................. | 73/104 |
| 2003/0217592 A1 * | 11/2003 | Nagaike et al. ............... | 73/104 |
| 2004/0187565 A1 * | 9/2004 | Sutton .......................... | 73/104 |
| 2005/0112115 A1 * | 5/2005 | Khan ........................ | 424/130.1 |
| 2006/0005613 A1 * | 1/2006 | Kuwajima et al. ............. | 73/104 |
| 2006/0169032 A1 * | 8/2006 | Sutton .......................... | 73/64.52 |

FOREIGN PATENT DOCUMENTS

JP    2003-240681 A    8/2003

* cited by examiner

*Primary Examiner*—Hezron E. Williams
*Assistant Examiner*—Samir M. Shah
(74) *Attorney, Agent, or Firm*—Knobbe Martens Olson & Bear

(57) ABSTRACT

A method of evaluating contact characteristics of an object having a roughness includes setting geometric shape data for the roughness; creating a roughness model and a structure model that comes in contact with the roughness, based on the geometric shape data set; making the roughness model and the structure model come in contact with each other; acquiring a physical amount occurring at least one of a contact region of the roughness model and a contact region of the structure model; and obtaining an evaluation value for evaluating a real contact state in the contact region between the roughness model and the structure model, from the physical amount acquired.

12 Claims, 27 Drawing Sheets

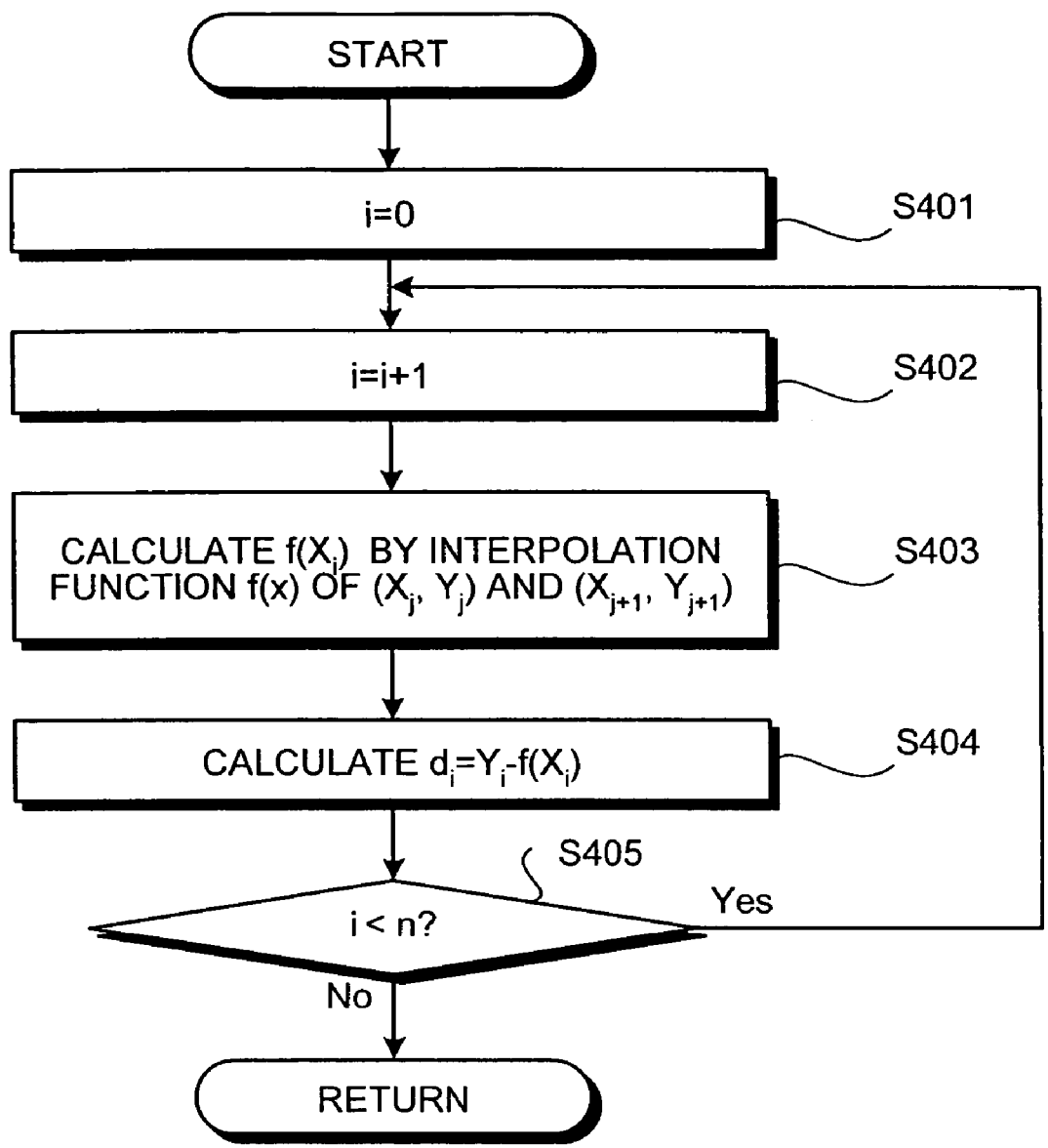

US 7,451,637 B2

METHOD OF EVALUATING CONTACT CHARACTERISTICS, AND COMPUTER PRODUCT

BACKGROUND OF THE INVENTION

1. Field of the Invention

The present invention relates to a method of evaluating contact characteristics of an object having a roughness.

2. Description of the Related Art

When friction characteristics between objects are discussed, it is essential to understand a contact state between the surfaces of the objects. In this case, it is important to understand a real contact state between the objects but not an apparent contact state. This case is also applied to a case where a contact state of a tire rolling along a road surface having irregularities. In other words, the friction characteristics and dynamic characteristics of the tire are evaluated, and when it is to be predicted, it is necessary to obtain details of the real contact state between the tire and the road surface as much as possible.

Japanese Patent Application Laid-Open (JP-A) No. 2003-240681 discloses a technology of setting a tire on a replica model of a road surface with a plurality of grooves formed thereon, measuring a depth of the tire that penetrates into a groove between projections of the replica model, and evaluating how the road surface and the tire contact each other. JP-A No. 2003-240681 also discloses a technology of evaluating how the road surface and the tire contact each other by bringing the tire into contact with the replica model that is manufactured with a transparent plate based on an actual road surface model, and observing a contact surface between the two from the opposite side of the contact surface.

However, in the technologies disclosed in JP-A No. 2003-240681, it is difficult to obtain the details of the real contact state of the contact surface between the road surface and the tire. Further, it is not easy to create and change the replica model of the road surface, and besides, it takes time and effort to evaluate the replica model.

SUMMARY OF THE INVENTION

It is an object of the present invention to at least solve the problems in the conventional technology.

A method of evaluating contact characteristics of an object having a roughness, according to one aspect of the present invention, includes setting geometric shape data for the roughness; creating a roughness model and a structure model that comes in contact with the roughness, based on the geometric shape data set; making the roughness model and the structure model come in contact with each other; acquiring a physical amount occurring at least one of a contact region of the roughness model and a contact region of the structure model; and obtaining an evaluation value for evaluating a real contact state in the contact region between the roughness model and the structure model, from the physical amount acquired.

A computer-readable recording medium according to another aspect of the present invention stores a computer program that causes a computer to execute the above method according to the present invention.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 21 is a flowchart of procedures for calculating a distance between a node of the structure model and the irregular surface model;

DETAILED DESCRIPTION OF THE PREFERRED EMBODIMENTS

Exemplary embodiments of the present invention are explained in detail below with reference to the accompanying drawings. It should be noted that the present invention is not limited by the preferred embodiments. Furthermore, components in the following embodiments include those which are thought of by persons skilled in the art or which are practically the same as the components. The present invention can be applied to a case where contact characteristics of a surface having roughness i.e. irregularities are evaluated. The present invention is preferably applied particularly to a case where a difference of rigidity between objects contacting each other is large. For example, such a case as explained above includes a relationship between the tread surface of a tire and a road surface and a relationship between a packing and a seal surface. Furthermore, it also includes a case where objects having irregular surfaces may be in contact with each other in their two irregular surfaces. The following explanation is performed using an example in which a road is an object whose surface has irregularities and a tire is a structure as an object that contacts the object, and using an example of evaluating contact characteristics between the tread surface of the tire and the road surface.

A method of evaluating contact characteristics according to an embodiment of the present invention is numerical simulation which has the features as follows. Data for geometric shape of the irregular surface of an object whose surface has irregularities is set, and an irregular surface model is created based on the data. A structure model that is discretely created is brought into contact with the surface of the irregular surface model, and physical amounts are acquired. The physical amounts include coordinates of nodes and force acting on each of the nodes or the like after deformation occurs in at least one of the structure model and the irregular surface model. Evaluation values on their contact state such as a real contact length, a real contact area, and the like are calculated from the physical amount. The method of evaluating contact characteristics according to the present embodiment is explained below.

Figure 1:
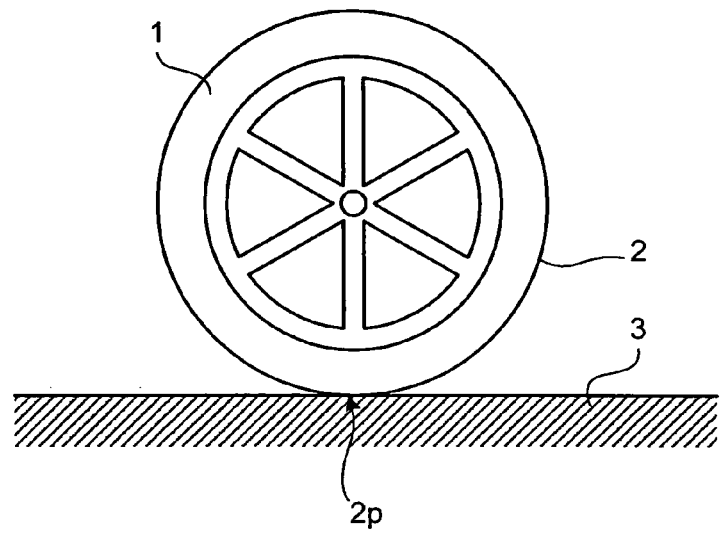
FIG. 1 is a diagram for explaining a state of a tire in contact with a road surface.
Figure 2:
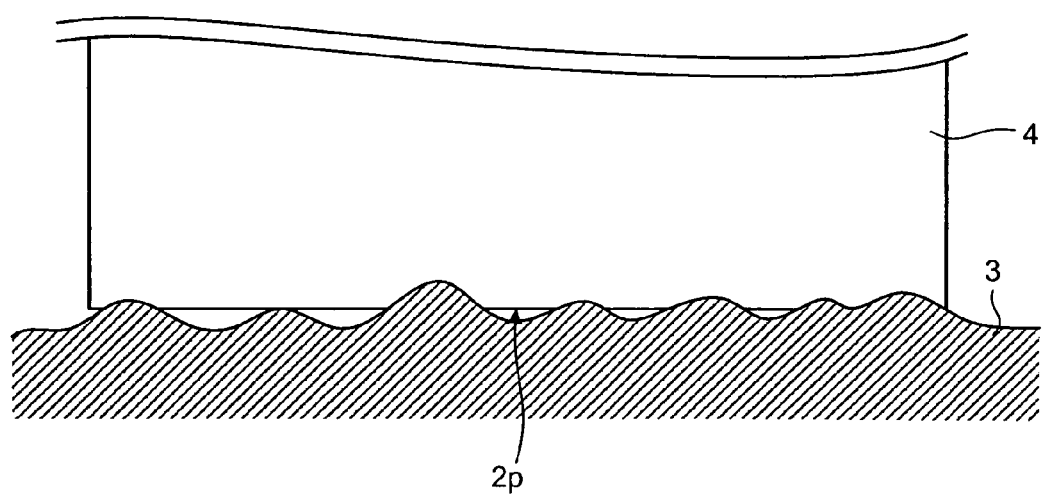
FIG. 2 is an enlarged diagram of a state of a block in contact with the road surface, the block forming a pattern of a tread surface of the tire.

FIG. 1 is a diagram for explaining a state of a tire in contact with a road surface. FIG. 2 is an enlarged diagram of a state of a block in contact with the road surface, the block forming a pattern of a tread surface of the tire. As shown in FIG. 1, a tire 1 contacts a road 3 at its tread surface 2p that forms a tread region 2. As shown in FIG. 2, the tread surface 2p of a block 4 that forms the tread region 2 contacts the surface of the road 3.

Figure 3A:
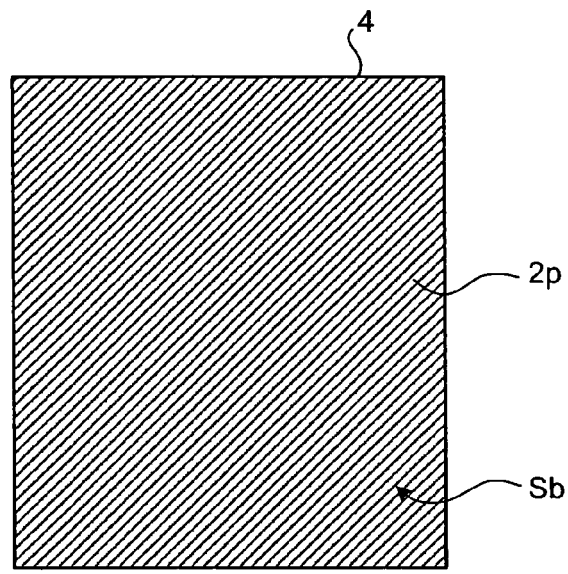
FIG. 3A is a plan view of an apparent contact area when viewed from a vertical direction with respect to the tread surface.
Figure 3B:
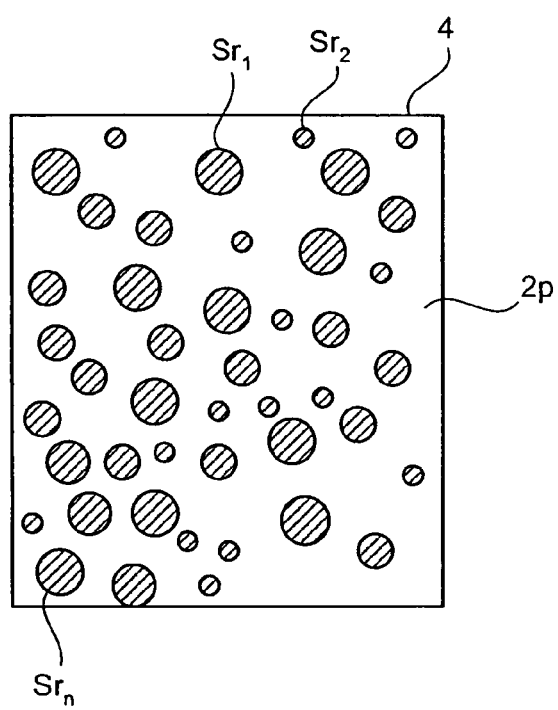
FIG. 3B is a plan view of a real contact area when viewed from the vertical direction with respect to the tread surface.

Generally, even when the objects contact each other, the whole of the contact surfaces is not always in contact with each other. If a contact portion is microscopically observed, it is found that a real contact area is smaller than an apparent contact area due to irregularities on the contact surface, i.e. roughness thereof. FIG. 3A is a plan view of the apparent contact area when viewed from a vertical direction with respect to the tread surface. FIG. 3B is a plan view of the real contact area when viewed from a vertical direction with respect to the tread surface.

Referring to a relationship between the tire and the surface of the road, as shown in FIG. 3A, it is ideal that the whole of the tread surface 2p contacts the road 3 and that the apparent contact area is supposed to be an area indicated by reference sign Sb. However, if a contact portion between the tread surface 2p and the road 3 is microscopically observed, it is found that the entire tread surface 2p of the block 4 does not always contact the road 3 because irregularities are formed on the surface of the road 3. Therefore, in actual cases, as shown in FIG. 3B, the respective projections formed on the surface of the road 3 contact the tread surface 2p of the block 4. A real contact area Sr between the tread surface 2p and the road 3 is expressed by a total sum of contact areas in the individual projections: $Sr=Sr_1+Sr_2+ \ldots +Sr_n$, where $Sr_n$ is a contact area between the individual projections and the tread surface. If mean peak height and mean valley depth of the irregular surface are the same level as each other, the following expression is generally obtained: $Sr<Sb$.

In order to evaluate the friction characteristics (tribology characteristics) between objects, it is important to obtain as accurately as possible how the objects contact each other, such as the size of a contact area, the magnitude of contact pressure, or distribution of the contact pressure. Referring to the contact with the surface having irregularities in particular, it is important to obtain a contact state of a real contact surface but not a contact state of an apparent contact surface. In order to evaluate the friction characteristics between the tire 1 and the road 3, it is also important to obtain the details of a contact state of the real contact surface between the tread surface 2p and the road 3 as much as possible and as accurate as possible. Therefore, the present invention employs a method as follows.

The method of evaluating contact characteristics (or a contact state) according to the present embodiment (hereinafter, "the method according to the present embodiment") is a numerical simulation using an analysis method such as a finite element method and a boundary element method. In this method, geometric shape data for the irregular surface of a road is set, and an irregular surface model is created based on the geometric shape data. A structure model that is created discretely is brought into contact with the surface having irregularities of the irregular surface model, and physical amount are acquired. The physical amount include coordinates of nodes and force acting on each of the nodes or the like after deformation occurs in at least one of the structure model and the irregular surface model. Evaluation values on their contact state such as a real contact length, a real contact area, and the like are calculated from the physical amount. The method according to the present embodiment is explained below.

Figure 4:
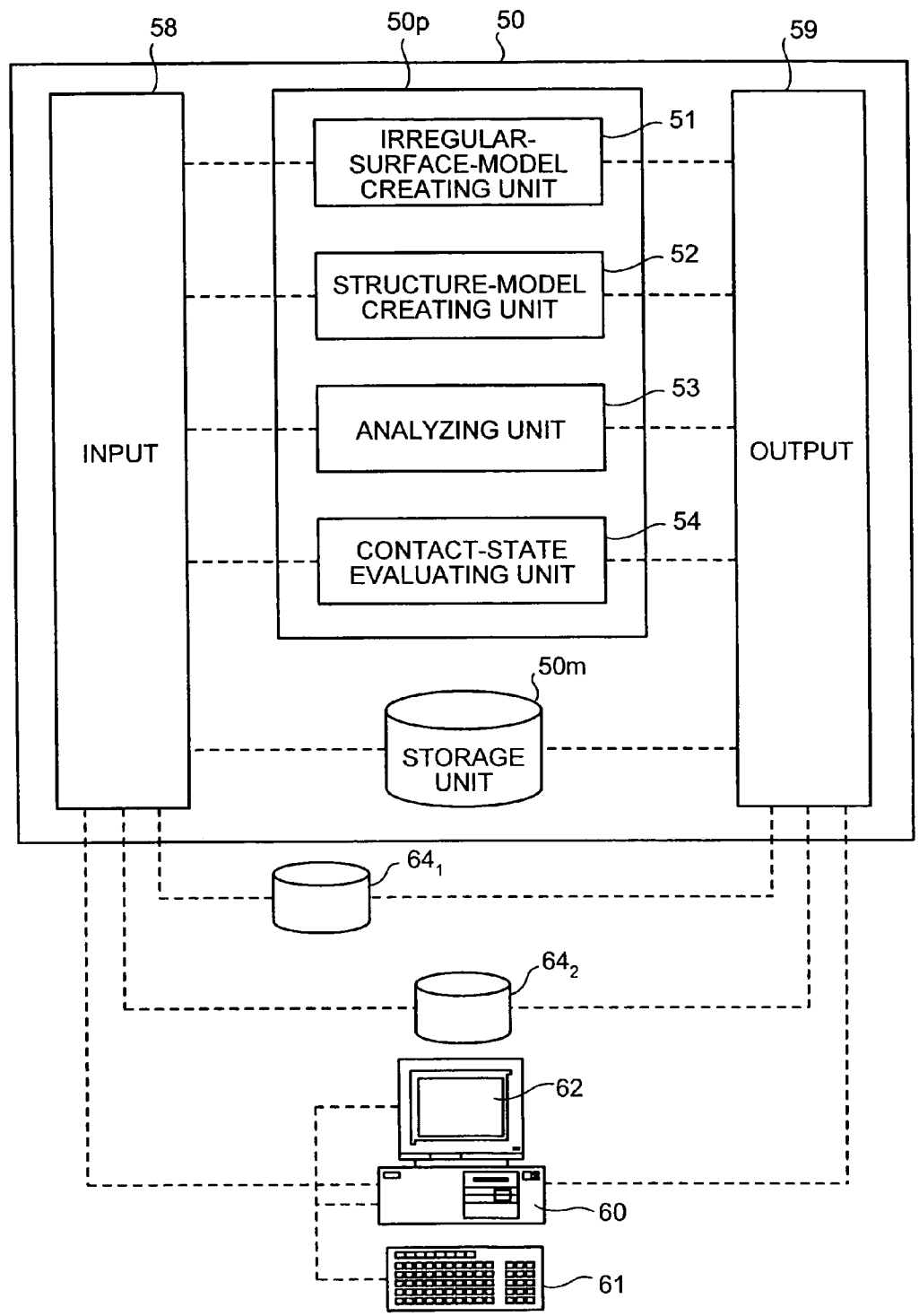
FIG. 4 is a diagram for explaining a configuration of an evaluation device for a contact state according to an embodiment of the present invention.

The method according to the present embodiment can be realized by using an evaluation device for a contact state according to the present embodiment. FIG. 4 is a diagram for explaining a configuration of the evaluation device for a contact state according to the present embodiment. The evaluation device for a contact state (hereinafter, "evaluation device") 50 includes a processor 50p and a storage unit 50m. The processor 50p and the storage unit 50m are connected to each other through an input port 58 and an output port 59.

The processor 50p includes an irregular-surface-model creating unit 51, a structure-model creating unit 52, an analyzing unit 53, and a contact-state evaluating unit 54. These components implement the method according to the present embodiment. The irregular-surface-model creating unit 51, the structure-model creating unit 52, the analyzing unit 53, and the contact-state evaluating unit 54 are connected to the input port 58 and the output port 59 so as to mutually exchange data.

The input port 58 and the output port 59 are connected with a terminal device 60. The terminal device 60 transmits data required for implementing the method according to the present embodiment, to the evaluation device 50 through an input device 61 connected to the terminal device 60. The data transmitted is a physical-properties value of rubber and a physical-properties value of wheels that form the tire 1, or a boundary condition and a running condition used to analyze a rolling state. The terminal device 60 receives a result of evaluation for the contact state from the evaluation device 50, and displays the result on a display device 62 connected to the terminal device 60. The input port 58 and the output port 59 are further connected with a various-data server $64_1$ and a various-data server $64_2$. To implement the method according to the present embodiment, the configuration is provided so as to allow the processor 50p to use various databases stored in the various-data servers $64_1$ and $64_2$.

The storage unit 50m stores a computer program including process procedures for the method according to the present embodiment, and data such as physical properties of material acquired from the various-data servers $64_1$ and $64_2$. The data for the physical properties of material is used for implementing the method according to the present embodiment. Here, the storage unit 50m can be formed with a volatile memory such as Random Access Memory (RAM), a nonvolatile memory such as a flash memory, or a combination of these memories. The processor 50p can be formed with a memory and a central processing unit (CPU). Furthermore, the storage unit 50m may be built-in in the processor 50p or may be in another device such as a database server. The evaluation device 50 may access the processor 50p and the storage unit 50m from the terminal device 60 through communications.

The computer program may implement the process procedures for the method according to the present embodiment by being combined with another computer program that is already recorded in the irregular-surface-model creating unit 51 and the contact-state evaluating unit 54 or the like included in the processor 50p. The evaluation device 50 may also implement functions of the irregular-surface-model creating unit 51, the structure-model creating unit 52, the analyzing unit 53, and the contact-state evaluating unit 54 included in the processor 50p by using dedicated hardware, instead of the computer program.

The method according to the present embodiment can be implemented by causing a general-purpose computer or a computer system to load the computer program including the process procedures for this method and execute it. The term "computer system" mentioned here includes an operating system (OS) and hardware for peripheral devices. The procedures for implementing the method according to the present embodiment using the evaluation device 50 are explained below with reference to FIG. 1 to FIG. 4.

Figure 5:
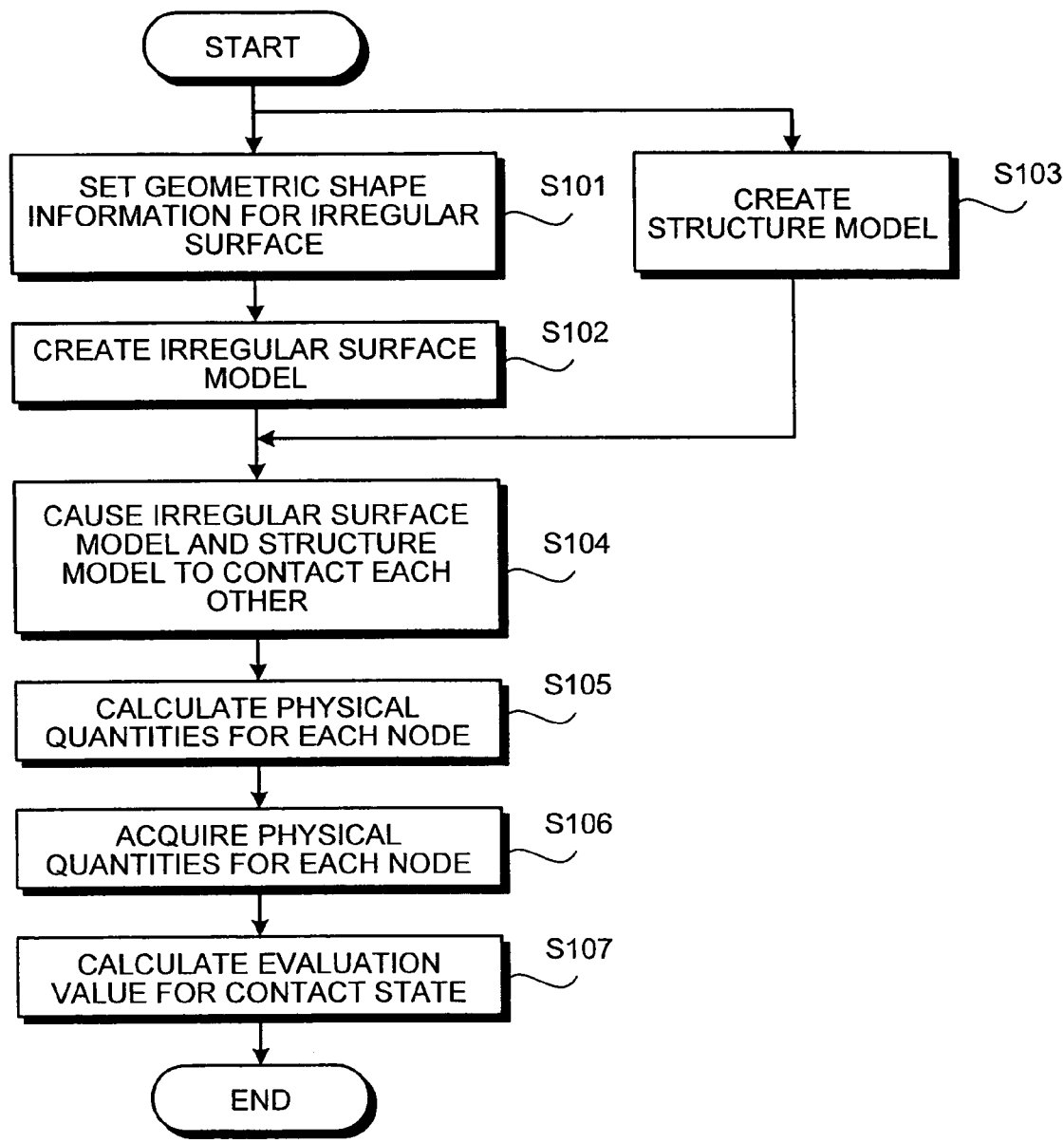
FIG. 5 is a flowchart of process procedures for a method of evaluatin contact characteristics according to the present embodiment.

FIG. 5 is a flowchart of process procedures for the method according to the present embodiment. To implement the method according to the present embodiment, geometric shape data for an irregular surface contacted by a structure is set (step S101). More specifically, the irregular surface indicates the surface of the road 3, and the structure indicates the block 4 of the tire 1 in this embodiment. The setting means setting of surface roughness of the irregular surface contacted by the structure. The geometric shape data for the irregular surface means data such as surface-profile parameters of a surface having irregularities. Although the surface of the road 3 is caused to have irregularities in this embodiment, the surface of the structure may also be caused to have irregularities. The method according to the present embodiment can be applied theoretically to any kinds of irregularities by changing a scale. For example, if applied to the case of simulation for a contact state between the road surface and the rubber, the method according to the present embodiment can preferably be used for an irregular surface which has a root mean square roughness Rq of about 1 micrometer to about 1000 micrometers.

For setting of the geometric shape data for the irregular surface, an actual irregular surface (e.g., a surface of an asphalt pavement and a surface of a concrete pavement) may be directly measured, or artificially created without actual measurement thereof. Furthermore, data measured is corrected and the geometric shape data for the irregular surface may be set using the data corrected. The example of directly measuring an actual road surface or the like is explained first.

Figure 6A:
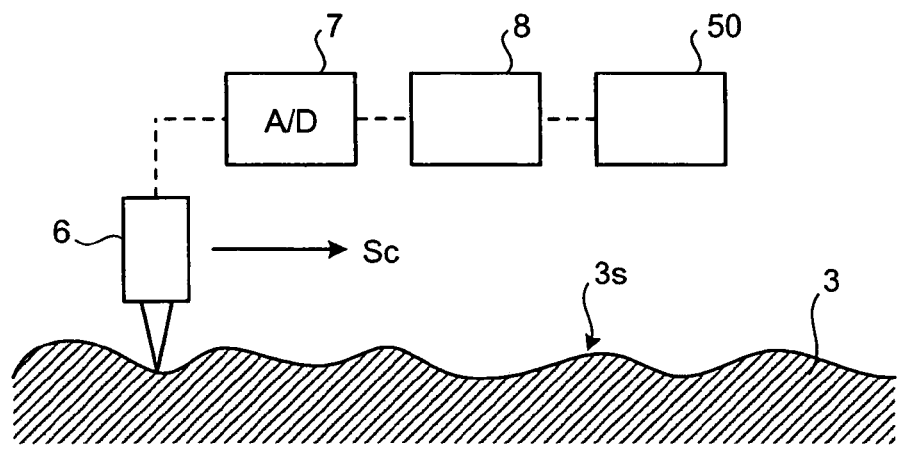
FIGS. 6A to 6C are diagrams for explaining an example of procedures for measuring an actual irregular surface and setting geometric shape data for the actual irregular surface.
Figure 6B:
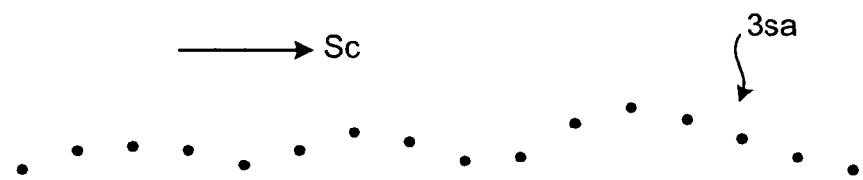
Figure 6C:
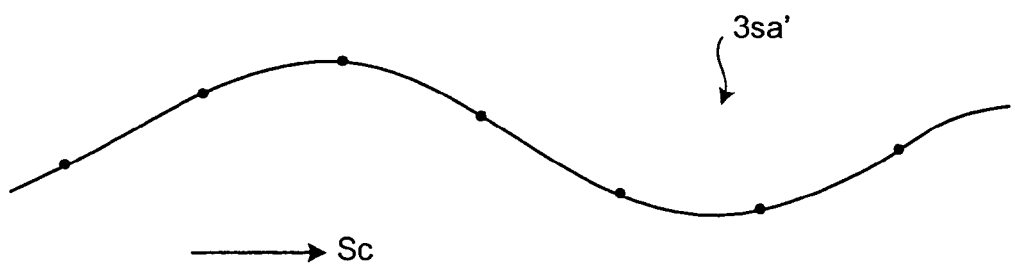

FIG. 6A to FIG. 6C are diagrams for explaining an example of procedures for measuring an actual irregular surface and setting geometric shape data for the actual irregular surface. At first, the actual irregular surface (surface 3s of the road 3 here) is measured. Data for the surface roughness obtained through measurement should only be two-dimensional or three-dimensional coordinate data. A measuring unit to be used includes a noncontact-type measuring unit such as a laser displacement sensor, and a contact-type measuring unit such as a stylus-type roughness measuring instrument. In this embodiment, a laser displacement sensor 6 is used to measure profile of the irregular surface of the road 3 in a noncontact method.

The laser displacement sensor 6 scans the surface of the road 3 to detect the irregularities on the surface of the road 3 at a fixed sampling frequency. The signal detected by the laser displacement sensor 6 is converted to a digital signal by an analog-to-digital converter (A/D converter), and is loaded in a computing unit 8. At this step, unnecessary noise may be removed from the data measured after being converted to the digital signal by removing slope and being subjected to filtering processing performed by a high-pass filter and a low-pass filter, or to averaging processing (e.g., moving average), and some other processing as necessary.

The data measured is converted to two-dimensional or three-dimensional coordinate data by the computing unit 8. FIG. 6B is a diagram of a coordinate data string 3sa of the irregular surface. This diagram shows that the coordinate data for the irregularities of the road 3 after the conversion is arranged along the scanning direction of the laser displacement sensor 6. As mentioned above, the laser displacement sensor 6 acquires data for the irregularities of the surface of the road 3 at the fixed sampling frequency. Therefore, the array of the coordinate data for the irregular surface acquired becomes discrete.

As shown in FIG. 6C, the coordinate data discretely acquired is subjected to function approximation to generate an irregular surface function 3sa' as required. This data generated is provided as geometric shape data for the irregular surface, i.e. the surface of the road 3. Although the function to be approximated is not particularly specified, a desirable function is such that it can express profile features of the surface irregularities of the road 3 as a target for measurement, as accurately as possible. For example, a trigonometric function or a periodic function similar to the trigonometric function, or a combination of polynomials can be used for a two-dimensional cross section. When the geometric shape data for the surface of the road 3 that is an irregular surface is to be subjected to function-approximation, the whole region over the surface of the road 3 may be function-approximated. Alternatively, a part of the surface of the road 3 may be partially function-approximated. For example, only a periphery of a portion of the irregular surface of the road 3 in contact with the tread surface 2p of the tire 1 is partially function-approximated. By partially function-approximating the irregular surface in the above manner, it is possible to simplify the geometric shape data for the surface of the road 3. It is noted that the coordinate data itself discretely obtained may be provided as geometric shape data for the road 3.

Based on the procedures, it is possible to measure the actual irregular surface and set the geometric shape data for the irregular surface. When the geometric shape data for the irregular surface is set based on the actual measurement, this setting is sent to the irregular-surface-model creating unit 51 included in the processor 50p in the evaluation device 50. The irregular-surface-model creating unit 51 uses the geometric shape data for the irregular surface received for processes at the following steps.

Figure 7A:
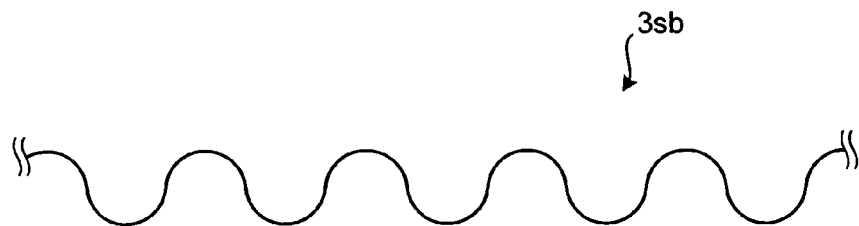
FIGS. 7A to 7D are diagrams for explaining an example of geometric shape data for an irregular surface generated by combining arbitrary geometric shapes.
Figure 7B:
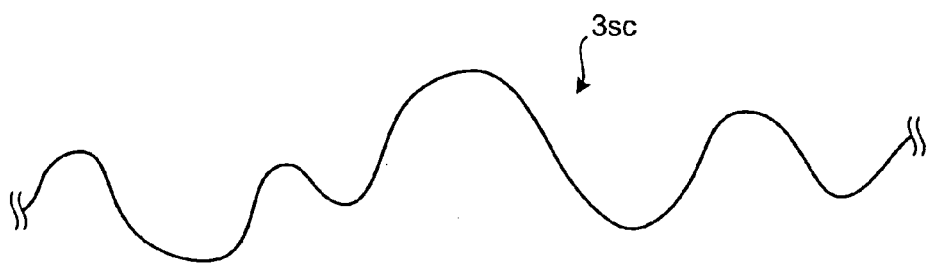
Figure 7C:
Figure 7D:
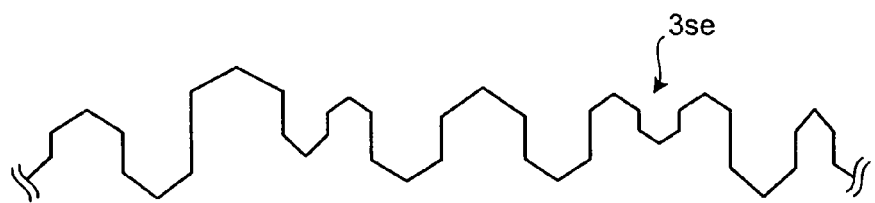

The method of generating geometric shape data for the irregular surface by combining arbitrary geometric shapes without actual measurement is explained below. FIG. 7A to FIG. 7D are diagrams for explaining examples of geometric shape data for irregular surfaces generated by combining arbitrary geometric shapes. Here, FIG. 7A to FIG. 7D indicate a case where geometric shape data for the irregular surfaces is two-dimensionally expressed. For example, an irregular surface 3sb as shown in FIG. 7A is an example of generating the geometric shape of the irregular surface by combining semicircles. In this case, as shown in an irregular surface 3sc of FIG. 7B, the size of the semicircle to be combined may be changed according to locations to more accurately reproduce the profile of actual irregularities. As shown in irregular surfaces 3sd and 3se of FIG. 7C and FIG. 7D, the geometric shape of the irregular surface may be generated by combining not only the semicircle but also a triangle, a rectangle, and any other polygon. In addition to these, the geometric shape of the irregular surface may be generated using a trigonometric function and a periodic function similar to the trigonometric function. Furthermore, if the geometric shape data for the irregular surface is three-dimensionally expressed, the geometric shape data for the irregular surface may be generated by combining a polygon, a pyramid, a cone, a sphere, a semisphere, and the like.

By generating the geometric shape data for the irregular surface in combination of arbitrary geometric shapes in the above manner, it is possible to reduce time and effort required for the actual measurement of the irregular surface. When the geometric shape data for the irregular surface is to be generated by combining arbitrary geometric shapes, the irregular-surface-model creating unit 51 provided in the processor 50p for the evaluation device 50 generates it. If a general-purpose computer or a computer system is to implement the computer program including the process procedures for the method according to the present embodiment, the general-purpose computer or the like generates the geometric shape data for the irregular surface. In each case, by implementing a computer program including a function of selecting the type and the size of arbitrary geometric shapes used to form the irregular surface and combining the geometric shapes, it is possible to generate the geometric shape data for the irregular surface.

In the method according to the present embodiment, an analysis model of the irregular surface explained later is generated based on the geometric shape data for the irregular surface measured or generated. Then, the structure or an analysis model of material and another object, each of which is an object as a target for contact, is brought into contact with the analysis model of the irregular surface, and physical amount occurring on the contact surface between the two are acquired. The physical amount allows detailed evaluation of a real contact state between a surface having irregularities i.e. roughness and a smooth surface or between surfaces having roughness.

Figure 8A:
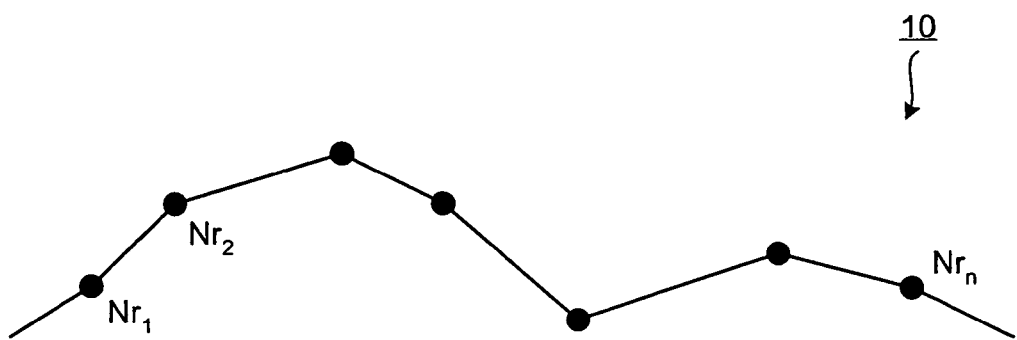
FIG. 8A is a diagram for explaining an example of an irregular surface model.
Figure 8B:
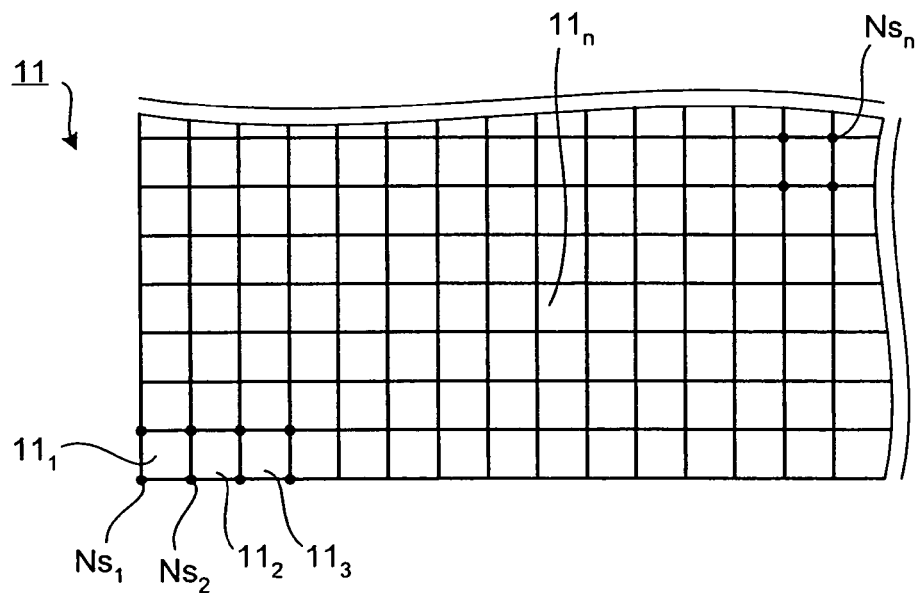
FIG. 8B is a diagram for explaining an example of a structure model.

FIG. 8A is a diagram for explaining an example of the irregular surface model. FIG. 8B is a diagram for explaining an example of the structure model. After the surface roughness of the irregular surface contacted by the structure is set (step S101), the irregular-surface-model creating unit 51 creates an irregular-surface analysis model 10 (which is an analysis model of the road 3, hereinafter, "irregular surface model 10") used for analysis (step S102). The structure-model creating unit 52 creates a structure analysis model 11 (which is an analysis model of the tire 1, hereinafter, "structure model 11") used for analysis (step S103). The irregular surface model 10 and the structure model 11 are analysis models used for analysis in the analysis method used in the method according to the present embodiment. It is noted that the order of processes among the creation of the geometric shape data for the irregular surface, the creation of the irregular surface model, and the creation of the structure model is not-particularly specified.

In the method according to the present embodiment, the finite element method (FEM) is used for the analysis method that is used to evaluate the contact state. The analysis method applicable to the method according to the present embodiment is not limited to the finite element method. Therefore, the boundary element method (BEM), a finite difference method (FDM), and the like can be used. It is also possible to use the most appropriate analysis method selected based on a boundary condition or so, or to use a plurality of analysis methods in combination. Since the finite element method is the analysis method suitable for structural analysis, it is appropriate for the case where the tire is selected as a structure in contact with an irregular surface.

To create the irregular surface model 10 and the structure model 11, the irregular surface model 10 and the structure model 11 suitable for the analysis method to be used are created so as to enable analysis using the analysis method such as the finite element method. When the finite element method is to be used, for example, as shown in FIG. 8A and FIG. 8B, the irregular surface and the tire which is a structure are segmented using nodes $Nr_1$, $Nr_2$, $Nr_n$, $Ns_1$, $Ns_2$, $Ns_n$ base on the finite element method. With this segmentation, for example, a model of the irregular surface is created by 2-node rigid body elements, and a model of the structure is created by dividing the structure into the finite elements $11_1$, $11_2$, $11_3$, and $11_n$.

The element based on the finite element method includes those as follows. For example, in a two-dimensional plane, a two-node shell and film, a rigid body element, a continuum element of a triangle and a rectangle can be used. In a three-dimensional space, a continuum element including a tetrahedral element, a pentahedral element, and a hexahedral element, a shell and a film element such as triangular and rectangular elements can be used. These elements are not particularly limited, and therefore, elements generally used for the finite element method can be used. The elements obtained through division in the above manner are specified one by one using the three-dimensional coordinates in the process of analysis.

Figure 9A:
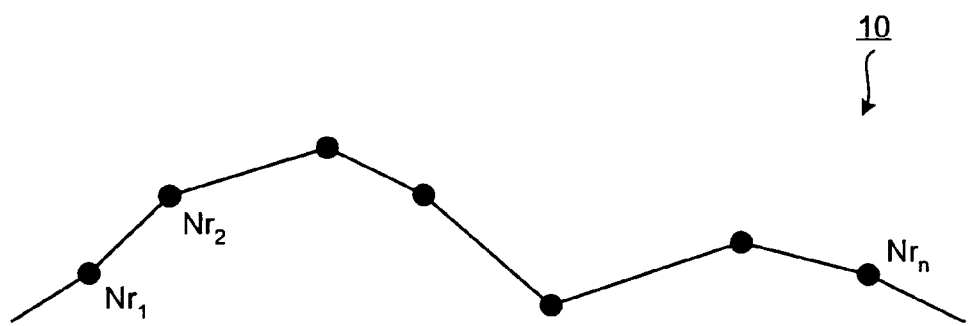
FIGS. 9A and 9B are diagrams for explaining a relationship between geometric shape data for an irregular surface and nodes of the irregular surface model.
Figure 9B:
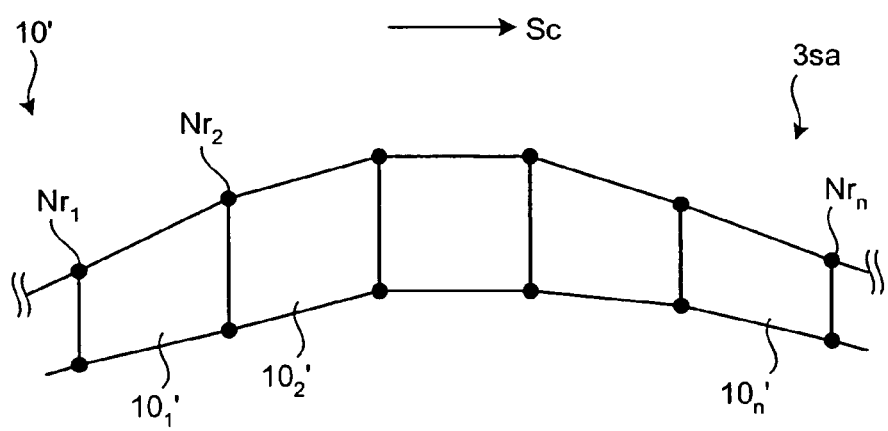

FIG. 9A and FIG. 9B are diagrams for explaining a relationship between the geometric shape data for the irregular surface and the nodes of the irregular surface model. The irregular surface model 10 is created based on the geometric shape data for the irregular surface set at step (step S101) at which the surface roughness of the irregular surface is set. Referring to the irregular surface model 10, the coordinate data itself for the geometric shape data for the road 3 discretely obtained may be used as nodes of the irregular surface model 10 (FIG. 9A). As shown in an irregular surface model 10', nodes of the irregular surface model 10' may be set from geometric shape data for the surface of the road 3 generated by function-approximating the coordinate data string 3sa for the irregular surface discretely obtained. The irregular surface models 10 and 10' may be created as a rigid body (rigid body element, rigid surface), or may be created as a modified body.

Figure 10A:
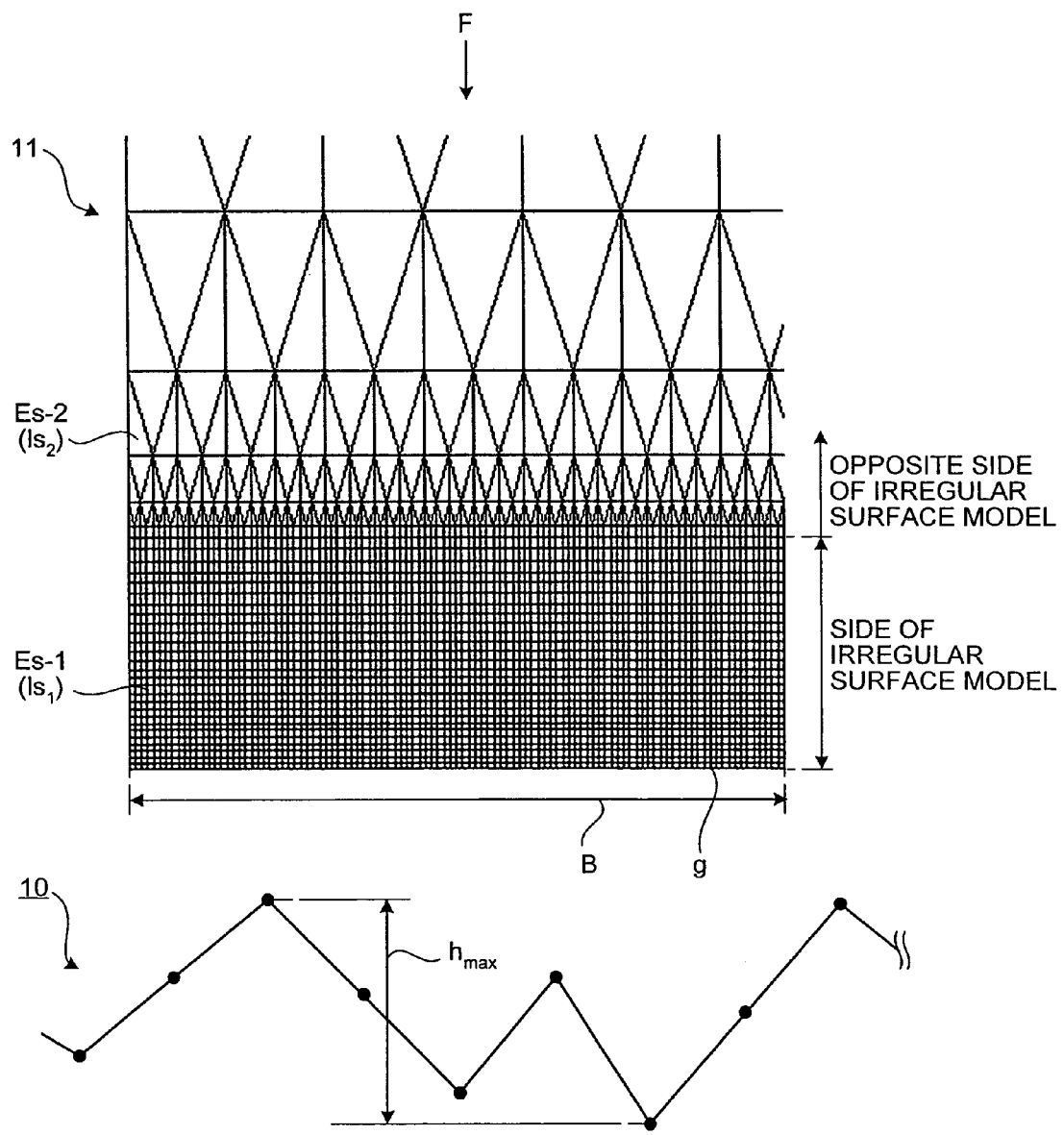
FIG. 10A is a conceptual diagram for explaining a relationship between elements that form the irregular surface model and elements that form the structure model.
Figure 10B:
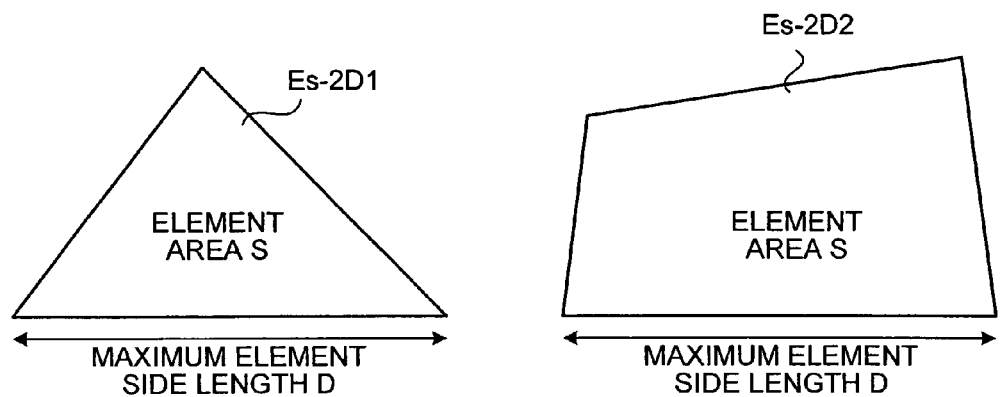
FIGS. 10B and 10C are diagrams for explaining dimensions of a typical element.
Figure 10C:
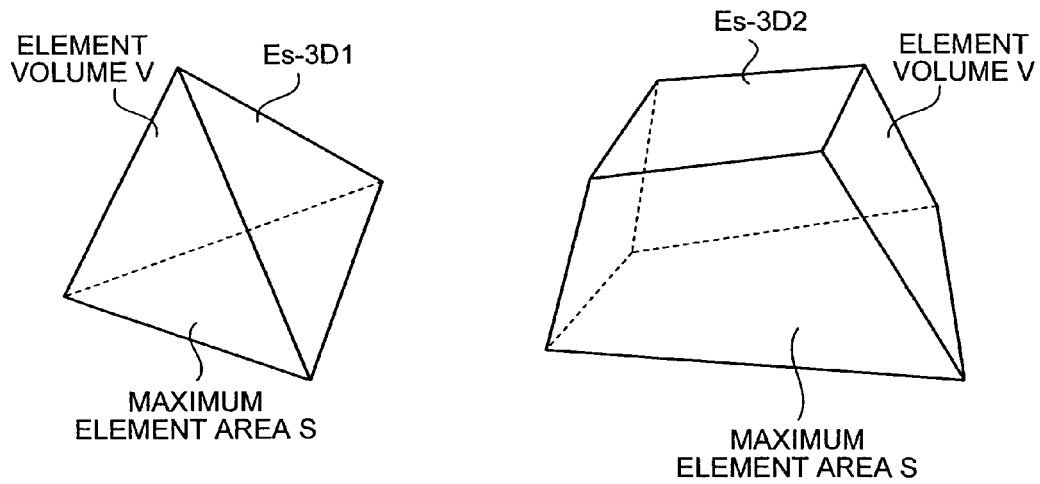

FIG. 10A is a conceptual diagram for explaining a relationship between elements that form the irregular surface model and elements that form the structure model. FIG. 10B and FIG. 10C are diagrams for explaining dimensions of typical elements. In these examples, first typical element dimensions $l_{s1}$ of an element Es-1 in an area of the structure model 11 on the side of the irregular surface model 10 is made smaller than second typical element dimensions $l_{s2}$ of an element Es-2 in an area thereof on the opposite side of the irregular surface model 10. In the numerical simulation related to the method according to the present embodiment, it is preferable for improvement of precision to make the typical element dimensions, such as the element Es-1 that forms the structure model 11, as small as possible as compared with the height of the irregularities of the irregular surface model 10. However, if the typical element dimensions of all the elements that form the structure model 11 are made smaller with respect to the height of the irregularities, calculation time increases. Therefore, in any part that is hardly affected by the irregularities due to contact with the irregular surface model 10, the second typical element dimensions $l_{s2}$ is made larger than the first typical element dimensions $l_{s1}$. In such a manner, the typical element dimensions of an element in an area that is largely affected by deformation due to the contact is made smaller than the typical element dimensions of an element in an area that is not much affected by deformation due to the contact. This allows improvement of precision of the simulation and minimization of increase in the calculation time.

An area of the structure model 11 on the side of the irregular surface model 10 mentioned in the present embodiment is a predetermined area from a profile line g of the structure model. More specifically, it indicates an area from the profile line g of the structure model up to a distance as twice as a maximum profile peak height $h_{max}$ of the irregular surface model 10. An area of the structure model 11 on the opposite side of the irregular surface model 10 is an area that is not the area of the structure model 11 on the side of the irregular surface model 10. The maximum profile peak height $h_{max}$ is calculated based on JIS B 0601.

If the structure model 11 is created two-dimensionally, the typical element dimensions are expressed by (element area)/(maximum element edge length) like two-dimensional elements Es-2D1 and Es-2D2 as shown in FIG. 10B. If the structure model 11 is created three-dimensionally, the typical element dimensions are expressed by (element volume)/(maximum element area) like three-dimensional elements Es-3D1 and Es-3D2 as shown in FIG. 10C.

It is preferable that the first typical element dimensions $ls_1$ are 0.5 times or less than the second typical element dimensions $ls_2$. This is because if the first typical element dimensions $ls_1$ are larger than 0.5 times the second typical element dimensions $ls_2$, the precision of the simulation rapidly decreases. From the viewpoint of maintaining the precision of the simulation at a predetermined level or higher, $ls_1 \leq 0.1 \times ls_2$ is more preferable. On the other hand, if $ls_1 < 0.001 \times ls_2$, the calculation time is largely increased. Therefore, from the viewpoint of minimizing the increase in the calculation time, $0.001 \times ls_2 \leq l_{s1}$ is preferable.

For the first typical element dimensions $ls_1$, an average value of the typical element dimensions of the elements Es-1 is used, the elements Es-1 being in the area of the structure model 11 on the side of the irregular surface model 10. Likewise, for the second typical element dimensions $ls_2$, an average value of the typical element dimensions of the elements Es-2 is used, the elements Es-2 being in the area on the opposite side of the irregular surface model 10. It is noted that a range in a direction perpendicular to a compression direction (direction indicated by arrow F of FIG. 10A) is a range (range indicated by B of FIG. 10A) in which the structure model 11 is in contact with the irregular surface model 10.

Figure 11A:
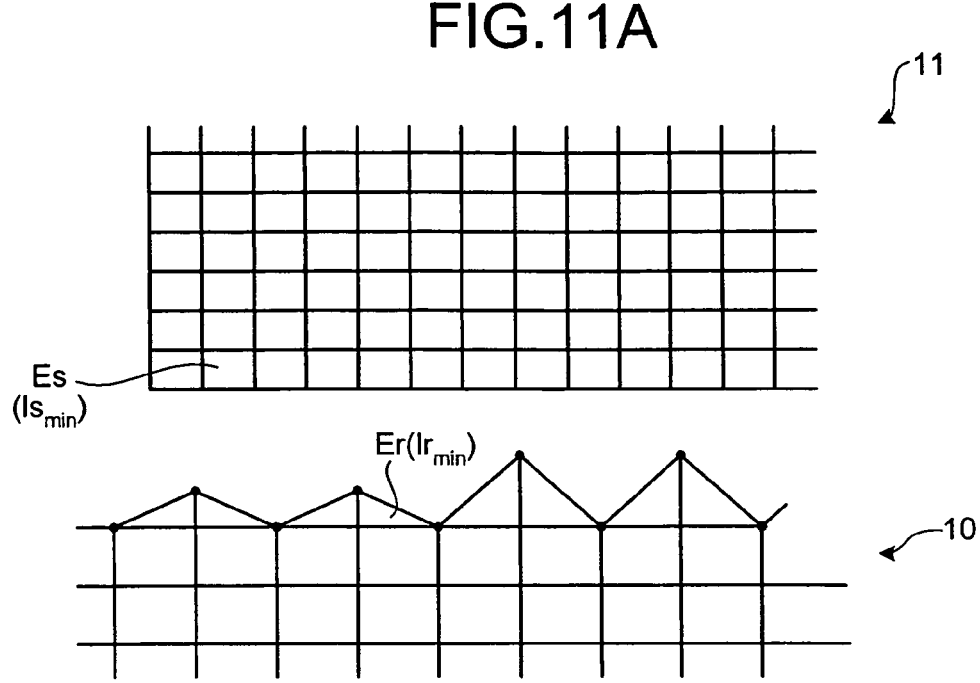
FIG. 11A is a diagram for explaining comparison between the elements of the structure model and the elements of the irregular surface model.
Figure 11B:
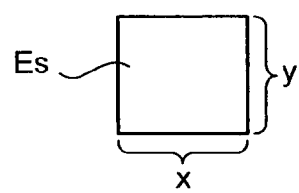
FIG. 11B is a diagram for explaining the element of the structure model.
Figure 11C:
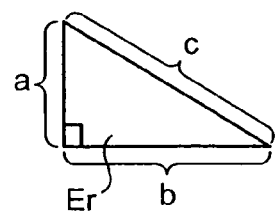
FIG. 11C is a diagram for explaining the element of the irregular surface model.

FIG. 11A is a diagram for explaining comparison between the elements of the structure model and the elements of the irregular surface model. FIG. 11B is a diagram for explaining one of the elements of the structure model. FIG. 11C is a diagram for explaining one of the elements of the irregular surface model. A minimum element of the elements that form the structure model 11 as shown in FIG. 11A is Es. A minimum element of the elements that form the irregular surface model 10 as shown in FIG. 11A is Er. In the present embodiment, structure-model minimum typical element dimensions $ls_{min}$ of the elements Es that form the structure model 11 is made to be equal to or less than irregular-surface-model minimum typical element dimensions $lr_{min}$ of the elements Er that form the irregular surface model 10. This is because the precision of the simulation is improved. If the structure-model minimum typical element dimensions $ls_{min}$ become less than 0.01 times the irregular-surface-model minimum typical element dimensions $lr_{min}$, a time increment ($\Delta t$) in an explicit method of the finite element method becomes too small, which causes the calculation time to largely increase. Therefore, the structure-model minimum typical element dimensions $ls_{min}$ range preferably from 0.01 times to 1 times the irregular-surface-model minimum typical element dimensions $lr_{min}$. Thus, it is possible to minimize the increase in the calculation time while improving the simulation precision.

A stable time increment ($\Delta t$) is explained below. In the finite element method, if the explicit method is used to simulate deformation, it is necessary that the time increment ($\Delta t$) satisfies the Courant condition. The Courant condition is expressed by $$\Delta t \leq L/\sqrt{(E/\rho)} \quad (1)$$

where $\Delta t$ is a time increment in the explicit method, L is a typical length of an element, E is elastic modulus, and $\rho$ is density. The Courant condition is determined for each element that forms the analysis model used for simulation, and a time increment of the whole analysis model is determined by an element having the minimum time increment of the analysis model. Therefore, if there is even one element that causes the time increment to be smaller in the analysis model, the time increment in the whole analysis model is caused to be smaller, which results in increase in an analysis time. Therefore, in the explicit method, it is extremely important to give careful attention to the elastic modulus and the density of materials and the division of the elements.

Figure 12:
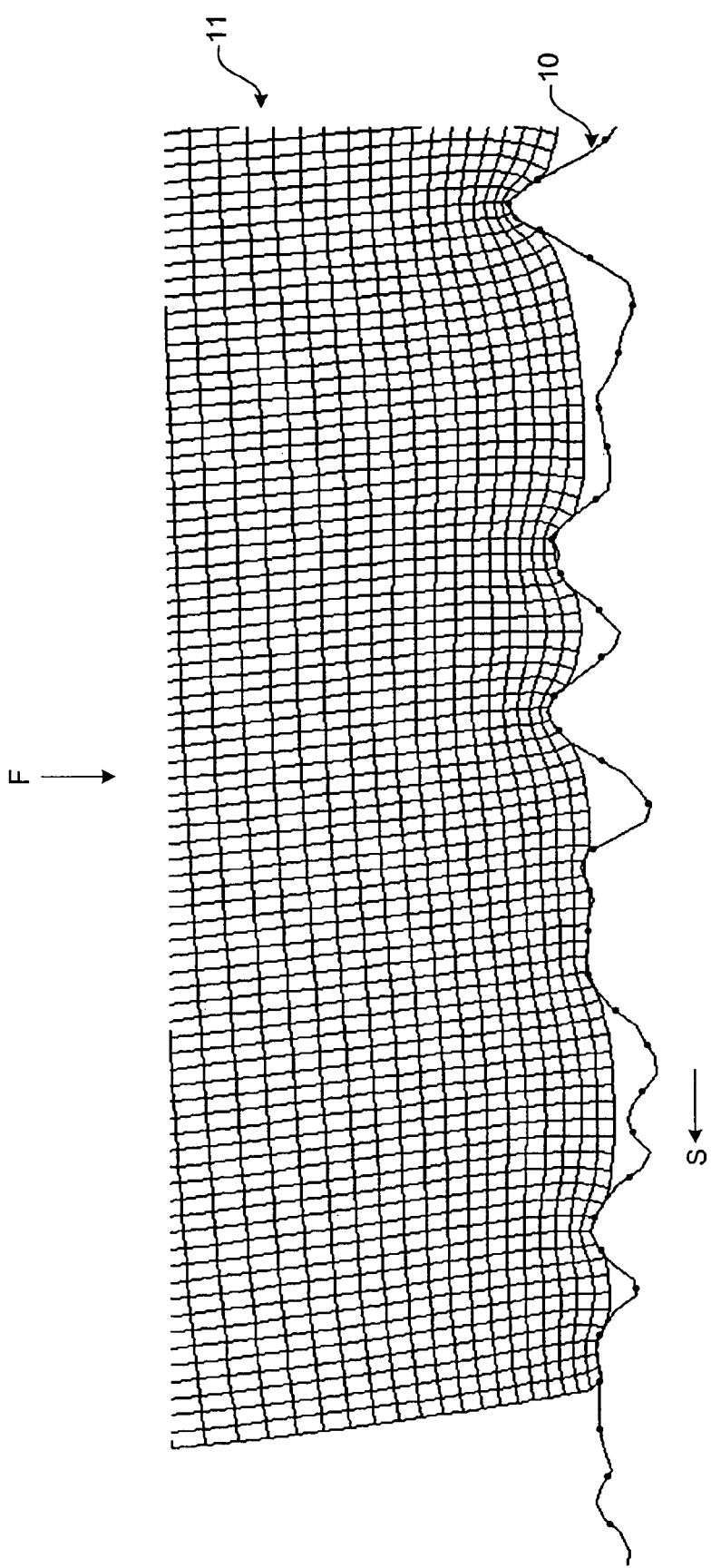
FIG. 12 is a diagram for explaining a state in which the irregular surface model and the structure model are brought into contact with each other.

FIG. 12 is a diagram for explaining a state in which the irregular surface model and the structure model are brought into contact with each other. After the irregular surface model 10 and the structure model 11 are created (steps S102, S103), the analyzing unit 53 causes the irregular surface model 10 and the structure model 11 to contact each other (step S104). For example, by applying a load or forcible displacement to both of the irregular surface model 10 and the structure model 11, these two can be brought into contact with each other. The direction of the load or the forcible displacement to be applied is not only the direction of compressing the structure model 11 as shown in FIG. 10A but also the direction in which shear deformation (direction indicated by arrow S of FIG. 12) may be applied after the load or the like is applied in the compression direction.

After the irregular surface model 10 and the structure model 11 are brought into contact with each other (step S104), the analyzing unit 53 calculates physical amount of nodes in at least one of the structure model 11 and the irregular surface model 10 after the contact (step S105). The physical amount include, for example, coordinates of nodes, force acting on each node, speed at each node, and acceleration at each node. Then, the contact-state evaluating unit 54 acquires physical amount of the nodes in at least one of the structure model 11 and the irregular surface model 10 after the contact (step S106), and calculates an evaluation value of the contact state based on the physical amount acquired (step S107). The evaluation value of the contact state includes a real contact length, a real contact area, and a contact pressure. The real contact length is used for two-dimensional analysis, and the real contact area is used for three-dimensional analysis.

When the irregular surface model 10 and the structure model 11 are in contact with each other (step S104), if the amplitude of the irregularities of the irregular surface model 10 is larger, the deformation (strain) of the structure model 11 becomes larger. In the method according to the present embodiment, the numerical simulation is used. Therefore, if the structure model 11 is largely deformed, it is sometimes impossible to carry out analysis caused by large deformation in its local portion. Therefore, elements present in the area of the structure model 11, which is deformed by the irregular surface model 10, are regenerated according to its deformation. With the regeneration, even if a local portion of the structure model 11 is largely deformed, the analysis can be continued. Particularly, if there is a large difference between the rigidity of the irregular surface model 10 and the rigidity of the structure model 11, by regenerating the elements, it is possible to reliably continue the analysis and improve analysis precision. For example, there is a case where an irregular surface corresponding to the rigidity of a paved road is made to contact a structure like elastomer such as rubber. This case corresponds to-the case of the large difference in rigidity as mentioned above. The case in which the difference in rigidity between objects to contact each other indicates that an object having a high rigidity (Young's modulus) has rigidity about 10 times as high as an object having a low rigidity. An example of such a combination as above includes a combination between the tire and the road.

Figure 13A:
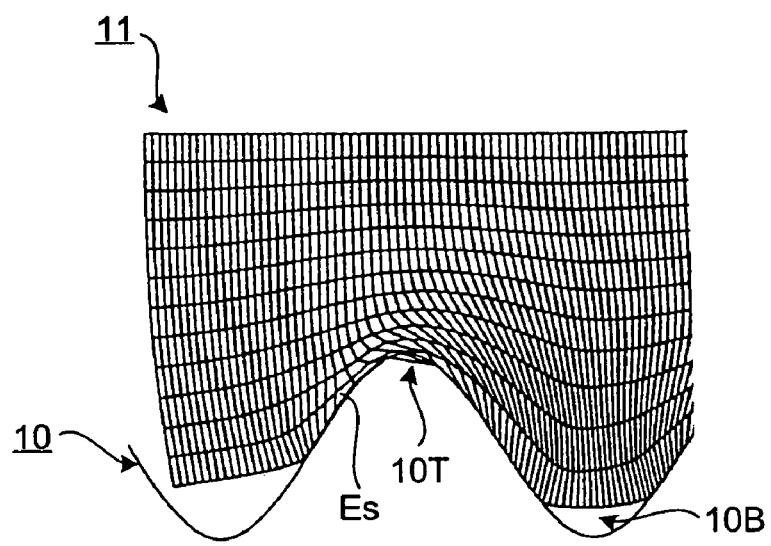
FIG. 13A is a diagram for explaining the structure model that is deformed by the contact with the irregular surface model.
Figure 13B:
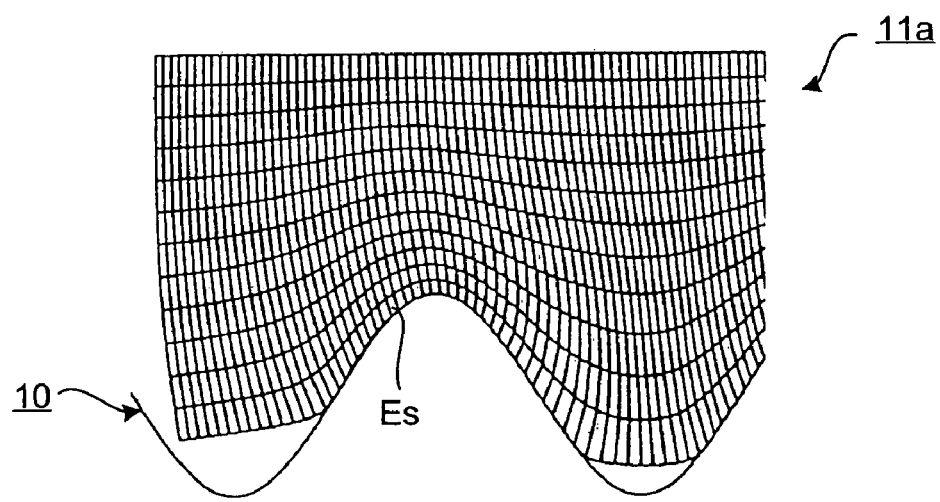
FIG. 13B is a diagram for explaining the structure model in which the elements deformed by the contact with. the irregular surface model are regenerated.

An example of a method of regenerating elements is explained below. FIG. 13A is a diagram for explaining the structure model that is deformed due to contact with the irregular surface model. FIG. 13B is a diagram for explaining the structure model in which the elements deformed due to contact with the irregular surface model are regenerated. As shown in FIG. 13A, when the structure model 11 comes in contact with the irregular surface model 10 and is thereby deformed, a portion in the structure model 11 near a peak 10T and a portion therein near a valley 10B of the irregularities are deformed too abnormally to continue calculation on the elements any further because the deformation of the shapes of the elements Es is so inappropriate for calculation. A method of solving the problem is as follows. That is, there is an effective method of newly regenerating the elements abnormally deformed and generating a modified structure model 11a (FIG. 13B).

Figure 14A:
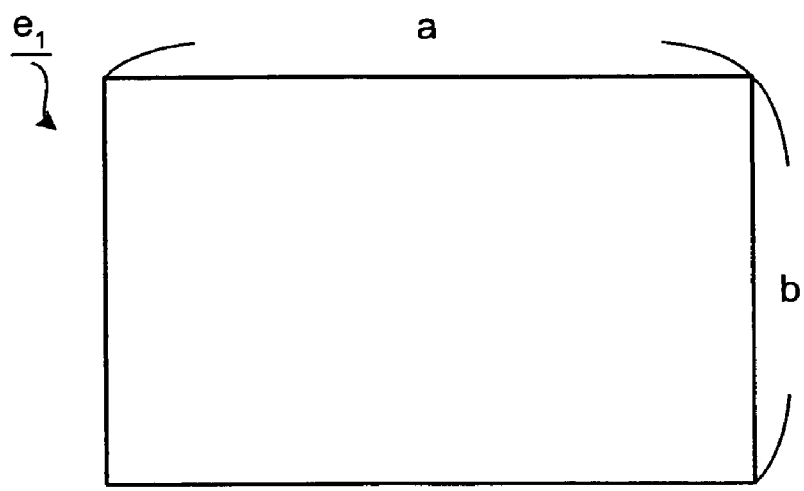
FIGS. 14A and 14B are diagrams for explaining a favorable element for analysis in the method of evaluating contact characteristics according to the present embodiment.
Figure 14B:
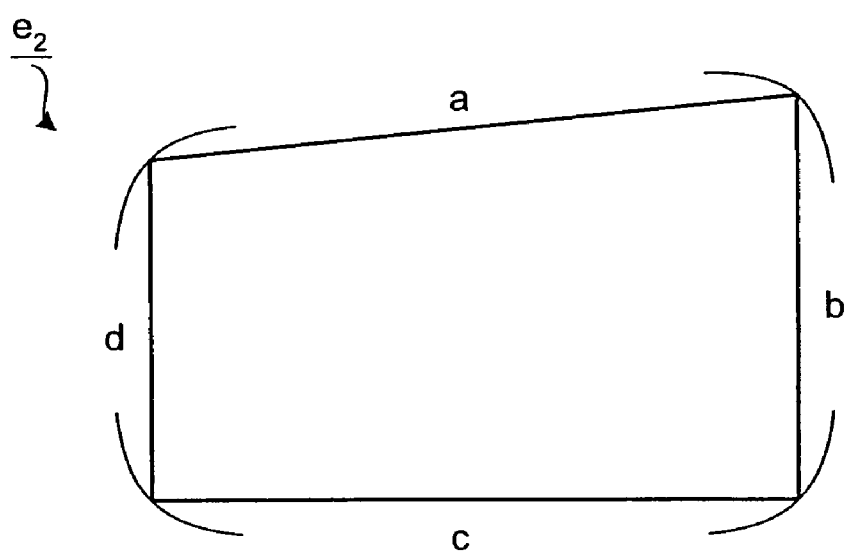
Figure 15A:
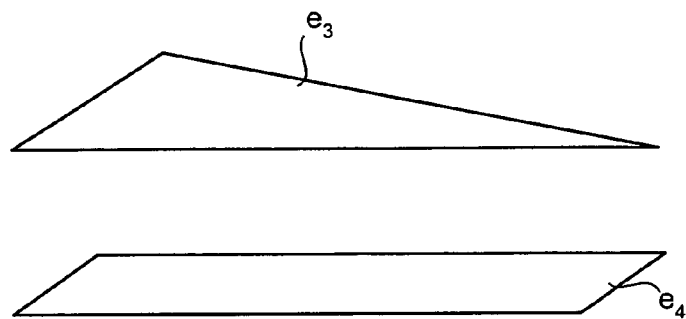
FIGS. 15A to 15C are diagrams for explaining an unfavorable element for analysis in the method of evaluating contact characteristics according to the present embodiment.
Figure 15B:
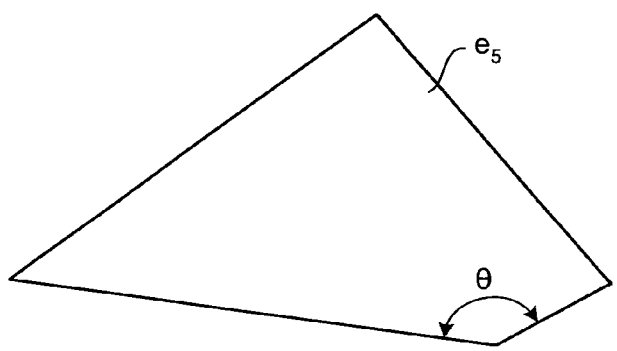
Figure 15C:
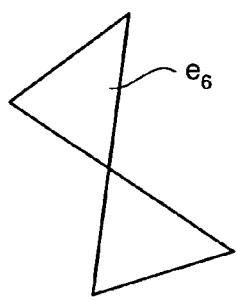

FIG. 14A and FIG. 14B are diagrams for explaining favorable elements for analysis in the method according to the present embodiment. FIG. 15A to FIG. 15C are diagrams for explaining unfavorable elements for analysis in the method according to the present embodiment. As shown in elements $e_1$ and $e_2$ of FIG. 14A and FIG. 14B, an element having an aspect ratio of approximately 1 is preferable for analysis in the method according to the present embodiment. Those as follows are included in the favorable case. More specifically, one of cases is such that the lengths of sides a and b are almost equal to each other and its shape is near a square (element $e_1$), and another one of the cases is such that the lengths of sides a, b, c, and d are almost equal to one another and its shape is near a square (element $e_2$)

On the other hand, if an element is abnormally deformed and dimensions of the element is extremely small as compared with dimensions of elements around the element, or if an aspect ratio of the element is large (FIG. 15A, elements $e_3$ and $e_4$), regeneration of the element is preferable by correcting the shape of the element and changing the type of the element through merging (integration) of nodes or resetting of internal nodes as required. Furthermore, if an interior angle of a part of an element is near 180 degrees (FIG. 15B, element $e_5$) and an element is twisted (FIG. 15C, element $e_6$), regeneration of the element is also preferable by changing the type of the element as required.

Abnormal deformation of an element can be determined referred to a typical element length, an aspect ratio, an interior angle of an element, an element area, and an element volume as indexes. Of these, the typical element length is a value obtained by dividing the element volume by the maximum area of an element surface (see FIG. 10C). Therefore, if an element has the typical element length of about 20% or less as compared with an average typical element length of an adjacent element group including the element, the element is preferably removed by merging (integrating) the nodes or so.

It is preferable that the aspect ratio of an element is near 1 as much as possible. More specifically, a range from 0.2 to 5.0 is preferable, and a range from 0.5 to 2.0 is more preferable. If the aspect ratio is beyond the range, it is preferable to remove the element by merging nodes or so. It is preferable that an interior angle of an element is near 90 degrees. More specifically, a range from 30 degrees to 150 degrees is preferable, and a range from 60 degrees to 120 degrees is more preferable. Particularly, if the interior angle of the element is beyond the range and near 180 degrees or beyond 180 degrees, it is preferable to divide again the element so as to divide the interior angle into two. How an element is twisted is determined preferably by obtaining its element area or its element volume. Any method known in the known finite element method can be applied to a method of obtaining the element area and the element volume.

Figure 16A:
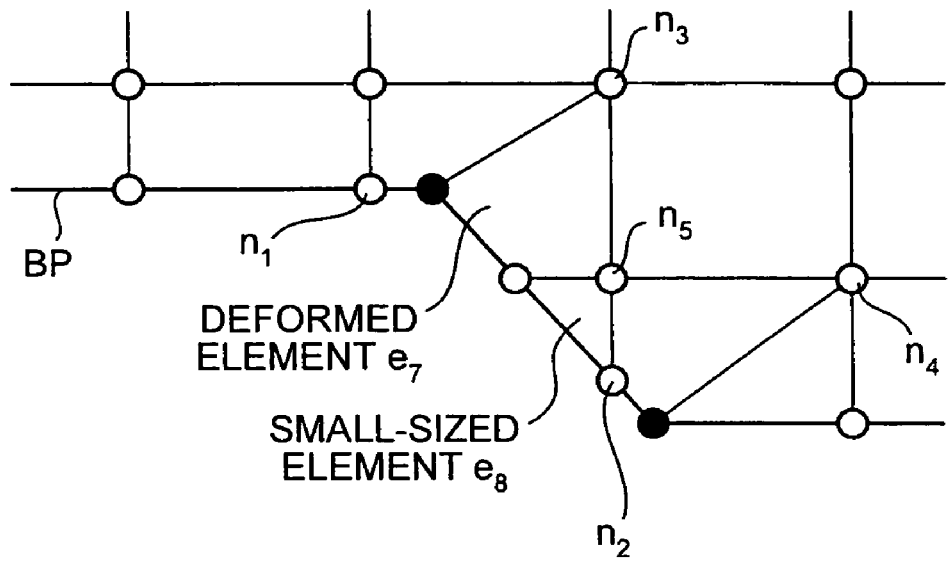
FIGS. 16A and 16B are diagrams for explaining an example of regenerating elements by resetting the internal nodes.
Figure 16B:
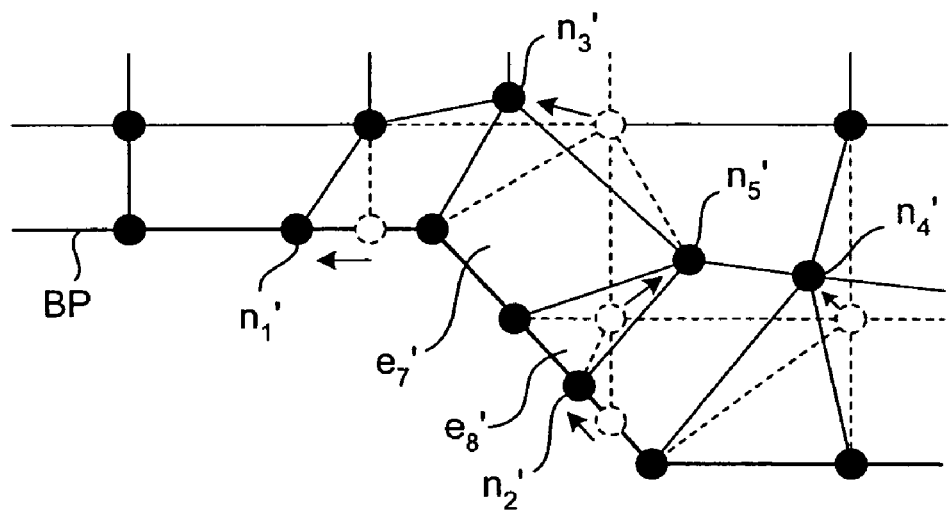

An example of regenerating an element by resetting internal nodes is explained below. FIG. 16A and FIG. 16B are diagrams for explaining examples of regenerating elements by resetting internal nodes. In these examples, a distorted element $e_7$ and a small-sized element $e_8$ as shown in FIG. 16A are regenerated. If nodes on each boundary surface BP are made to move in order to regenerate these elements, the small-sized element $e_8$ and the distorted element $e_7$ may sometimes be regenerated. In such cases, nodes $n_1$ and $n_2$ on the boundary surfaces. BP are made to move and internal nodes $n_3$, $n_4$, and $n_5$ are also made to move, and they are rearranged at positions of $n_1'$, $n_2'$, $n_3'$, $n_4'$, and $n_5'$ (FIG. 16A and FIG. 16B). Then, the small-sized element $e_8$ and the distorted element $e_7$ (FIG. 16A) are regenerated into an element $e_8'$ that has an allowable size and an element $e_7'$ of which aspect ratio is close to 1 (FIG. 16B). Thus, it is possible to suppress generation of a distorted element and a small-sized element cased by regeneration of elements.

Figure 17A:
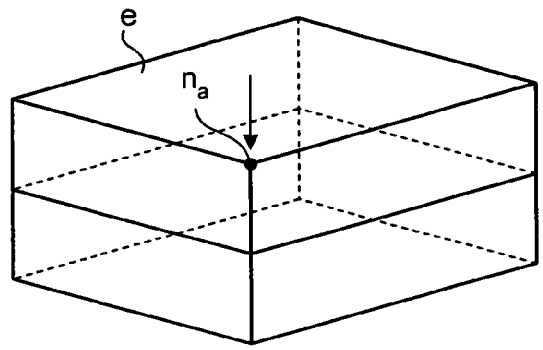
FIG. 17A is a diagram for explaining elements before their coordinates are changed for three-dimensional analysis.
Figure 17B:
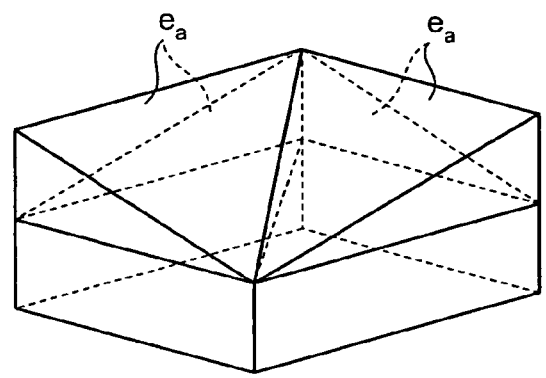
FIGS. 17B to 17F are diagrams for explaining an example of regenerating elements for the three-dimensional analysis.
Figure 17C:
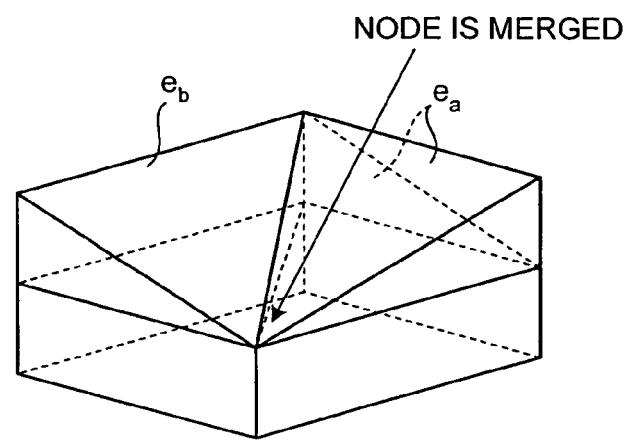

An example of regenerating an element for the three-dimensional analysis is explained below. FIG. 17A is a diagram for explaining elements before their coordinates are changed for three-dimensional analysis. FIG. 17B to FIG. 17F are diagrams for explaining an example of regenerating elements for the three-dimensional analysis. In the three-dimensional analysis, if an element e is deformed and only one node $n_a$ (FIG. 17A) of the node e is pressed down by the thickness of the element e, a combination of four tetrahedrons allows regeneration of the element e (FIG. 17B). At this time, as shown in FIG. 17C, the node $n_a$ (FIG. 17A) of the element e may be merged to regenerate the element e using a combination of two tetrahedrons $e_a$ and one pentahedral element $e_b$.

Figure 17D:
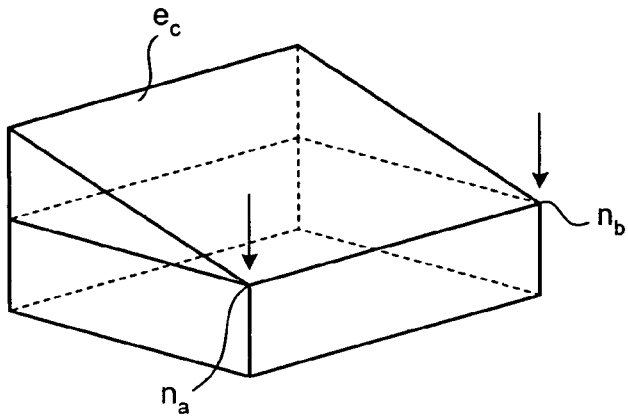
Figure 17E:
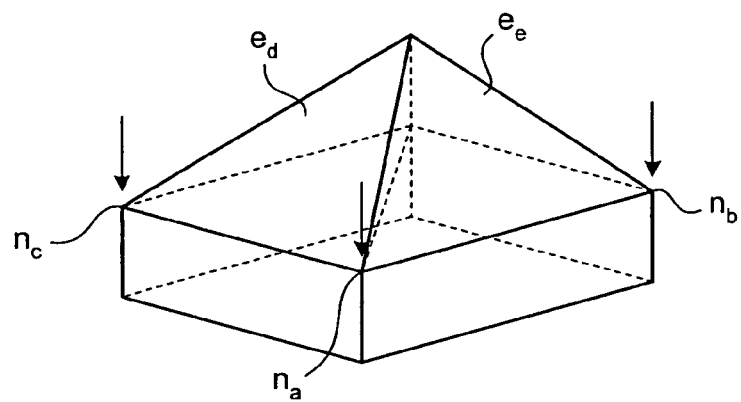
Figure 17F:
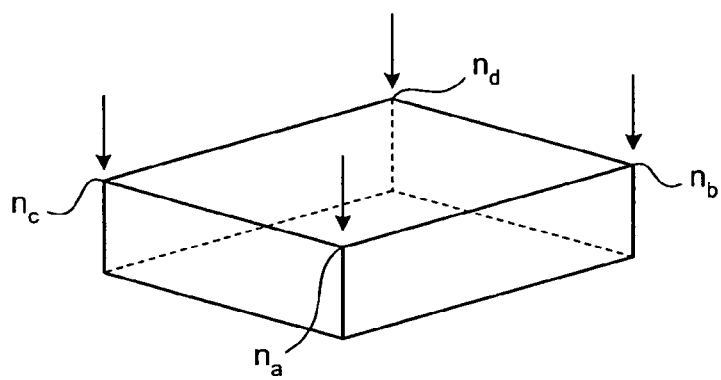

As shown in FIG. 17D, if two nodes $n_a$ and $n_b$ are pressed down by the thickness of the element e, the element e (FIG. 17A) is regenerated using one pentahedral element $e_c$. As shown in FIG. 17E, if three nodes $n_a$, $n_b$, and $n_c$ are pressed down by the thickness of the element e, the element e (FIG. 17A) is regenerated using two tetrahedral elements $e_d$ and $e_e$. As shown in FIG. 17F, if four nodes $n_a$, $n_b$, $n_c$, and $n_d$ are pressed down by the thickness of the element e, the element e (FIG. 17A) is removed. By using the method, it is necessary to change positions of nodes that form an element and reset the shape of the element abnormally deformed to a favorable shape.

Obtaining a real contact length or a real contact area between the irregular surface model and the structure model is essential to calculate an evaluation value of a contact state. Procedures for obtaining the real contact length or the real contact area are explained below. In the following explanation, the real contact length is obtained using the two-dimensional irregular surface model and structure model, but the real contact area using the three-dimensional irregular surface model and structure model can also be obtained in the same procedures.

Figure 18:
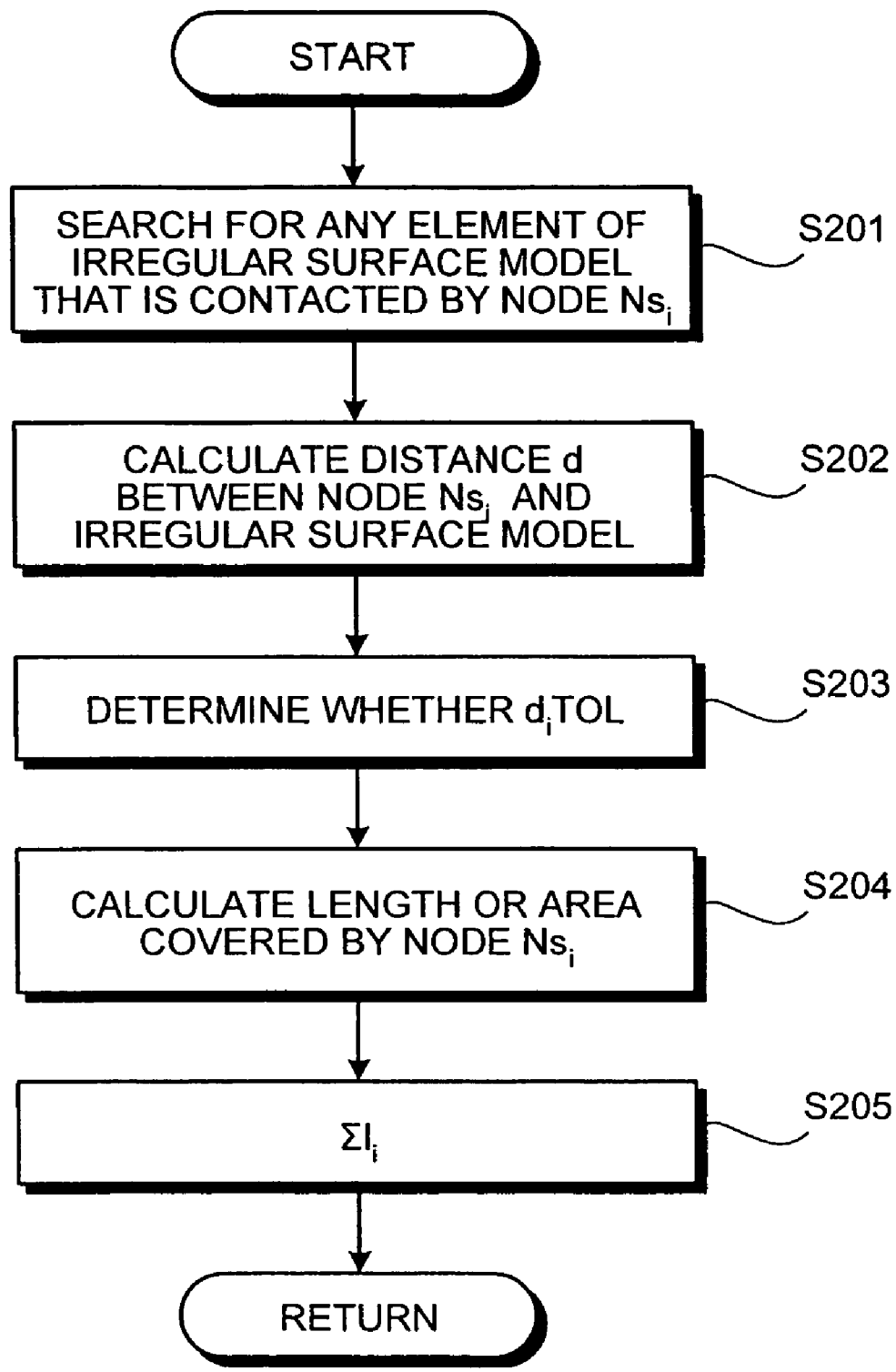
FIG. 18 is a flowchart of procedures for obtaining a real contact length according to the present embodiment.

FIG. 18 is a flowchart of procedures for obtaining the real contact length according to the present embodiment. In order to obtain the real contact length between the irregular surface model 10 and the structure model 11, the contact-state evaluating unit 54 searches for any element of the irregular surface model 10 that is in contact with a node of the structure model 11 (step S201). The procedures are explained below.

Figure 19A:
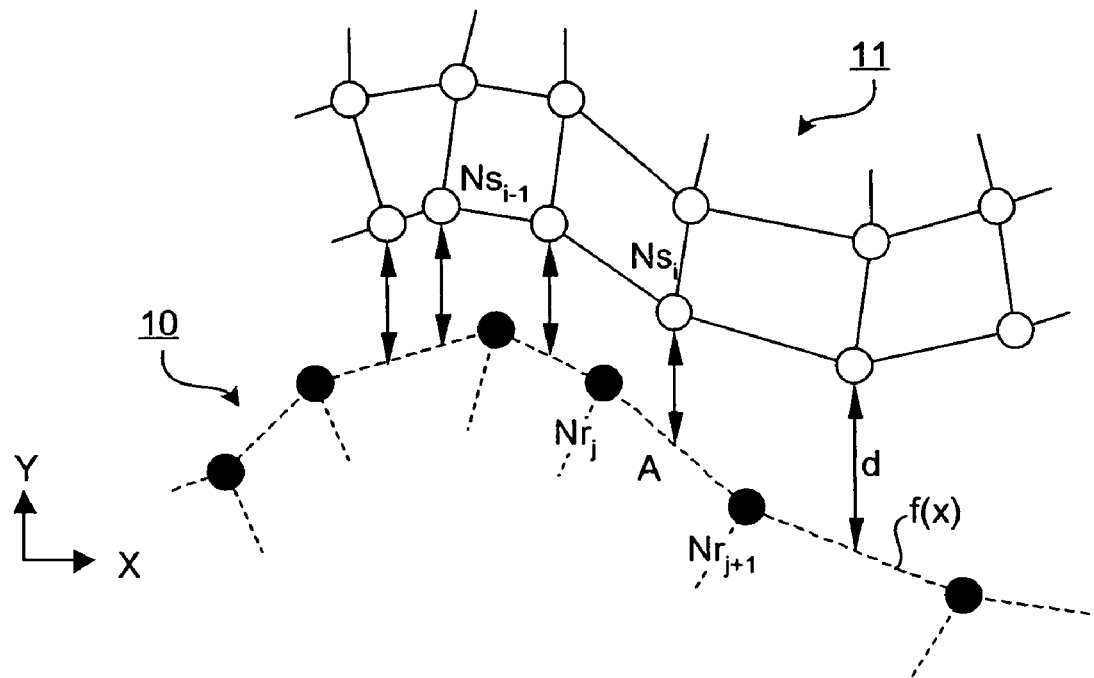
FIGS. 19A and 19B are diagrams for explaining a method of searching for any element of the irregular surface model that is contacted by a node of the structure model.
Figure 19B:
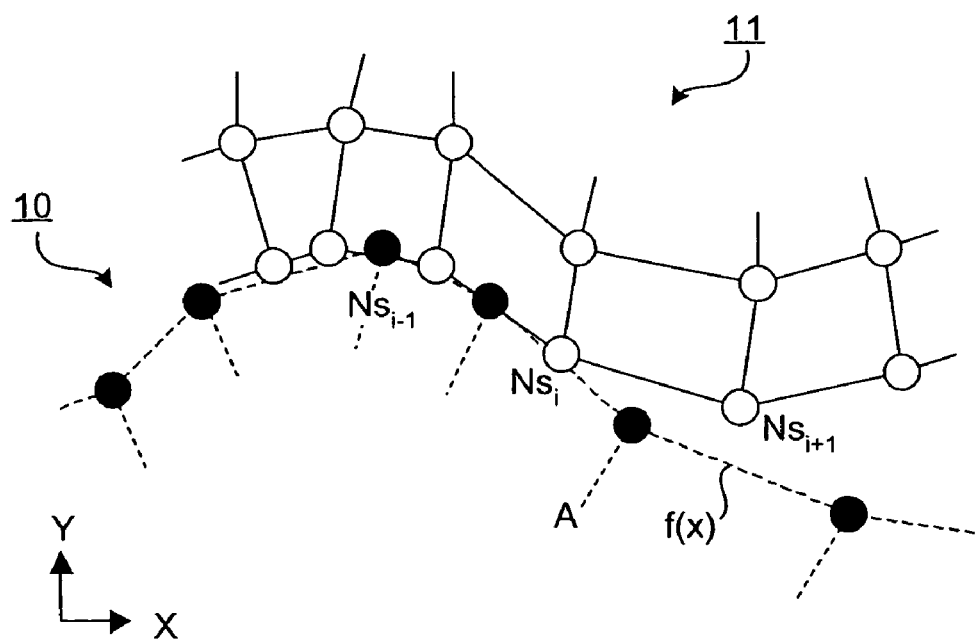
Figure 20:
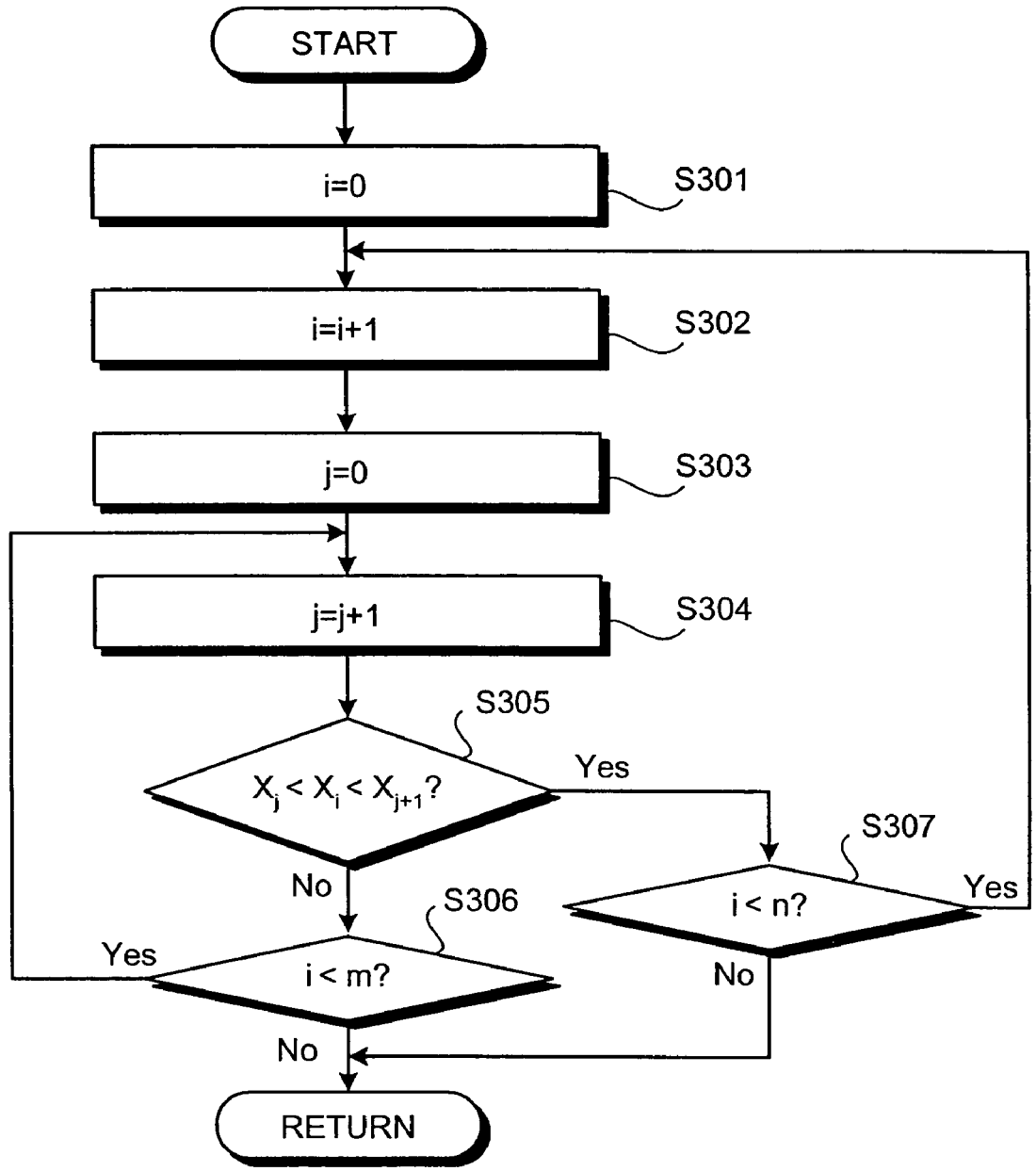
FIG. 20 is a flowchart of procedures for searching for any element of the irregular surface model that is contacted by a node of the structure model.

FIG. 19A and FIG. 19B are diagrams for explaining a method of searching for any element of the irregular surface model that is contacted by a node of the structure model. FIG. 20 is a flowchart of procedures for searching for an element of the irregular surface model contacted by a node of the structure model. At first, a variable indicating a node number is initialized to i=0 (step S301), and it is set to i=1 as an initial node (step S302). Then, in order to search for which position of the irregular surface is contacted by a node of the structure model, a variable indicating a road-surface element number is initialized to j=0 (step S303), and it is set to j=1 as an initial road-surface element (step S304).

FIG. 19A indicates a state where the irregular surface model 10 and the structure model 11 are close to each other. FIG. 19B indicates a state where the irregular surface model 10 and the structure model 11 are in contact with each other. The contact-state evaluating unit 54 determines which of surface elements of the irregular surface model 10 is contacted by a node $Ns_i$ of the structure model 11, or determines whether the node $Ns_i$ is included between adjacent node $Nr_j$ and node $Nr_{j+1}$ (step S305). If it is not included between segments j to j+1 (step S305; No), the contact-state evaluating unit 54 replaces an irregular-surface-element number j with j+1, and determines whether the node $Ns_i$ is in contact with an adjacent irregular surface element (step S306).

The contact-state evaluating unit 54 changes the irregular-surface-element number j from 1 to m−1 to search the irregular surface model 10. Then, the contact-state evaluating unit 54 searches for an element of the irregular surface model 10 that is $X_j < X_i < X_{j+1}$, and stores a correlation between the nodes of the structure model 11 and the elements of the irregular surface model 10 contacted by the nodes, where Xi is an X coordinate of the node $Ns_i$ on the surface of the structure model 11 and Xj is an X coordinate of the node $Nr_j$ on the irregular surface model 10.

Consequently, the contact-state evaluating unit 54 can determine between which nodes on the surface of the irregular surface model 10 the node $Ns_i$ of the structure model 11 is positioned. Therefore, it is possible to search for any element of the irregular surface model 10 that is contacted by the node of the structure model 11. In the examples of FIG. 19A and FIG. 19B, the node $Ns_i$ of the structure model 11 is positioned between the node $Nr_j$ and node $Nr_{j+1}$ on the surface of the irregular surface model 10 ($X_j < X_i < X_{j+1}$). In other words, the node $Ns_i$ of the structure model 11 is in contact with an element A of the irregular surface model 10.

The contact-state evaluating unit 54 searches for nodes on the surface of the irregular surface model 10, between which each of all nodes $Ns_i$ to $Ns_n$ on the surface of the structure model 11 in contact with the irregular surface model 10 is positioned (step S307; Yes). After the search is finished (step S307; No), the contact-state evaluating unit 54 stores a correlation between the nodes on the surface of the irregular surface model 10 searched for and the nodes on the surface of the structure model 11, in the storage unit 50m.

After the element of the irregular surface model 10 that is contacted by the node of the structure model 11 is searched for (step S201), the contact-state evaluating unit 54 calculates a distance $d_i$ between the node $Ns_i$ on the surface of the structure model 11 and the surface of the irregular surface model 10 (hereinafter, "inter-surface distance $d_i$") (step S202). FIG. 21 is a flowchart of procedures for calculating a distance between a node of the structure model and the irregular surface model. The contact-state evaluating unit 54 obtains an interpolation function f(x) for the node $Nr_j(X_j, Y_j)$ on the surface of the irregular surface model 10. The inter-surface distance $d_i$ can be obtained from a difference between the Y coordinate (=$Y_i$) of the node $Ns_i$ on the surface of the structure model 11 and the Y coordinate on the surface of the irregular surface model 10 that corresponds to the X coordinate (=$X_i$) of the node $Ns_i$. The latter half can be obtained by giving x=$X_i$ to the interpolation function f(x). That is, f($X_i$) is obtained.

The contact-state evaluating unit 54 sets the number of node counts i of the structure model 11 to i=0 (step S401). Then, the contact-state evaluating unit 54 sets the number of node counts i to i=i+1 (step S402). In this stage, because i=0 is set at step S401, the number of node counts i at step S402 becomes 1. The contact-state evaluating unit 54 gives $X_i$ to the interpolation function f(x) to obtain f($X_i$) (step S403), and obtains the inter-surface distance $d_i$=$Y_i$-f($X_i$) (step S404). The contact-state evaluating unit 54 executes the procedures to all the nodes $Ns_i$ on the surface of the structure model 11 (step S405; Yes), and obtains each inter-surface distance $d_i$ for all the nodes $Ns_i$ (step S405; No)

Figure 22A:
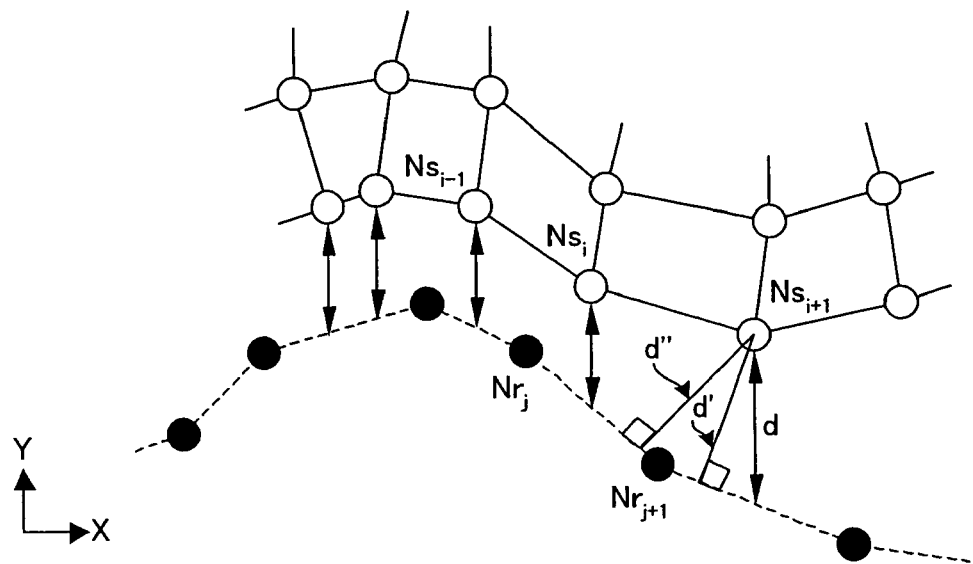
FIGS. 22A and 22B are diagrams for explaining an example of how to obtain an inter-surface distance.
Figure 22B:
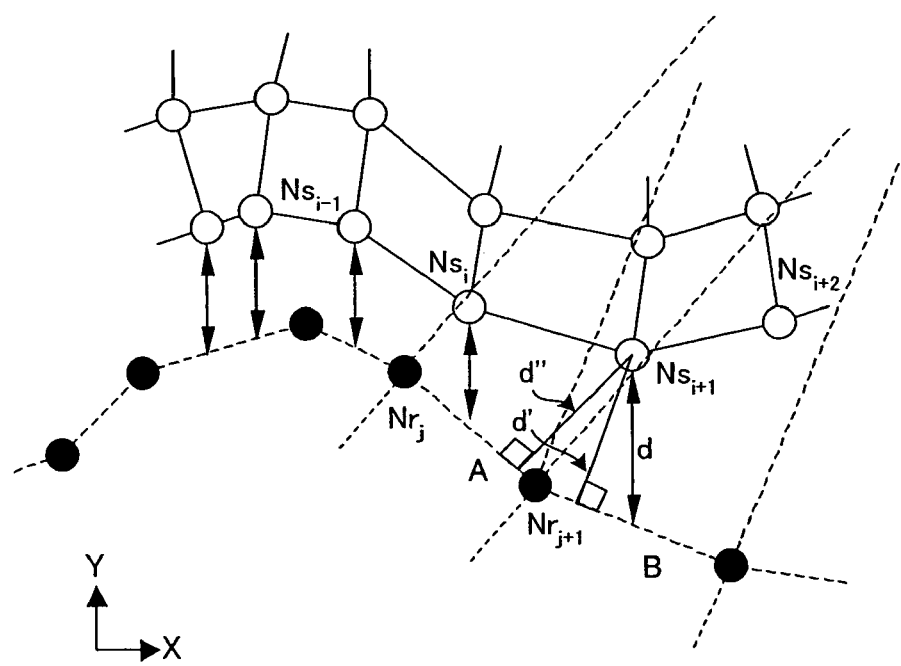

FIG. 22A and FIG. 22B are diagrams for explaining examples of how to obtain an inter-surface distance. A relative movement between the structure model 11 and the irregular surface model 10 is not always only in the Y direction of FIG. 22A and FIG. 22B. Therefore, the inter-surface distance may be obtained using a method as explained below. As shown in FIG. 22A and FIG. 22B, nodes on the surface of the structure model 11 included in a range of normals toward the structure model 11 are $Ns_i$ and $Ns_{i+1}$, from the nodes $Nr_j$ and $Nr_{j+1}$ of the element A of the irregular surface model 10. Nodes on the surface of the structure model 11 included in a range of normals toward the structure model 11 are $Ns_{i+1}$ and $Ns_{i+2}$, from nodes $Nr_{j+1}$ and $Nr_{j+2}$ of an element B of the irregular surface model 10. Therefore, the node $Ns_{i+1}$ on the surface of the structure model 11 is included in both of the element A and the element B.

In this case, inter-surface distances d" and d' from the node $Ns_{i+1}$ on the surface of the structure model 11 toward the element A and the element B of the irregular surface model 10 are obtained, respectively. The inter-surface distance is the shortest distance form the node $Ns_{i+1}$ to the element A or the element B (FIG. 22B). A shorter one of the inter-surface distances d" and d' is set to an inter-surface distance d between the node $Ns_{i+1}$ on the surface of the structure model 11 and the surface of the irregular surface model 10.

The contact-state evaluating unit 54 determines whether the inter-surface distance $d_i$ is smaller than a predetermined allowed value TOL, and determines whether the node $Ns_i$ on the surface of the structure model 11 is in contact with the surface of the irregular surface model 10 (step S203). In this determination, an absolute value of the inter-surface distance $d_i$ is compared with the predetermined allowed value TOL. This is because even if the node $Ns_i$ on the surface of the structure model 11 and the inter-surface distance $d_i$ of the irregular surface model 10 are actually in contact with each other, the inter-surface distance $d_i$ does not always become 0 due to a rounding error of a numerical value or some other causes according to the nature of the numerical simulation.

Figure 23:
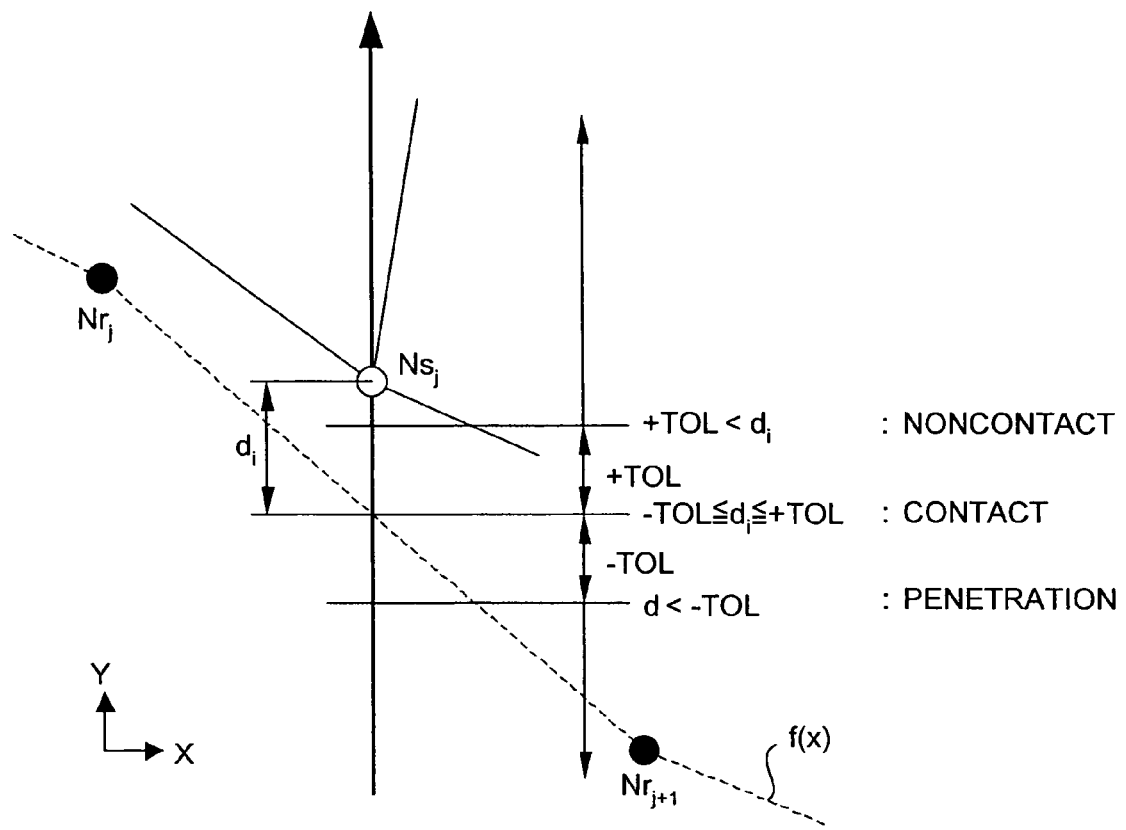
FIG. 23 is a diagram for explaining a concept of determining whether a node on the surface of the structure model is in contact with the surface of the irregular surface model.

FIG. 23 is a diagram for explaining a concept of determining whether a node on the surface of the structure model is in contact with the surface of the irregular surface model. If $|d_i|$<TOL, namely, if -TOL$\leq d_i \leq$+TOL, the contact-state evaluating unit 54 determines that the node $Ns_i$ on the surface of the structure model 11 is in contact with the surface of the irregular surface model 10. In this case, the contact-state evaluating unit 54 stores data such that the node $Ns_i$ is in contact with the surface of the irregular surface model 10, in the storage unit 50m.

If +TOL$\leq d_i$, the contact-state evaluating unit 54 determines that the node $Ns_i$ is not in contact with the surface of the irregular surface model 10. If $d_i \leq$-TOL, the contact-state evaluating unit 54 determines that the node $Ns_i$ penetrates into a portion between projections of the irregular surface model 10. In both cases, the node $Ns_i$ on the surface of the structure model 11 is not in contact with the surface of the irregular surface model 10, and therefore, such a node as above on the surface of the structure model 11 covers neither the length nor the area of an element. The contact-state evaluating unit 54 stores data for the node on the surface of the structure model 11 which is not in contact with the surface of the irregular surface model 10, in the storage unit 50m.

Figure 24:
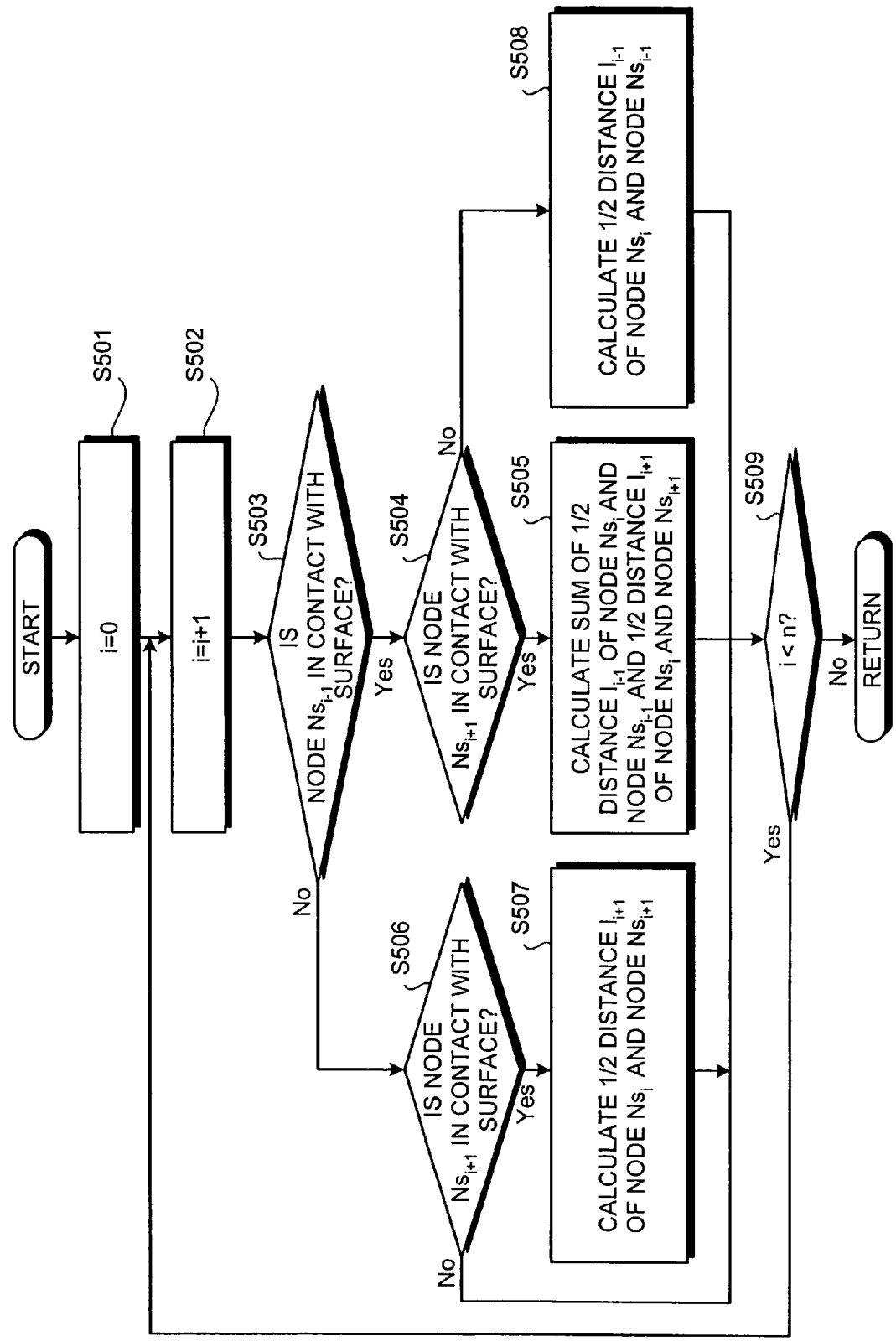
FIG. 24 is a flowchart of procedures for obtaining a length covered by a node on the surface of the structure model in contact with the surface of the irregular surface model.
Figure 25:
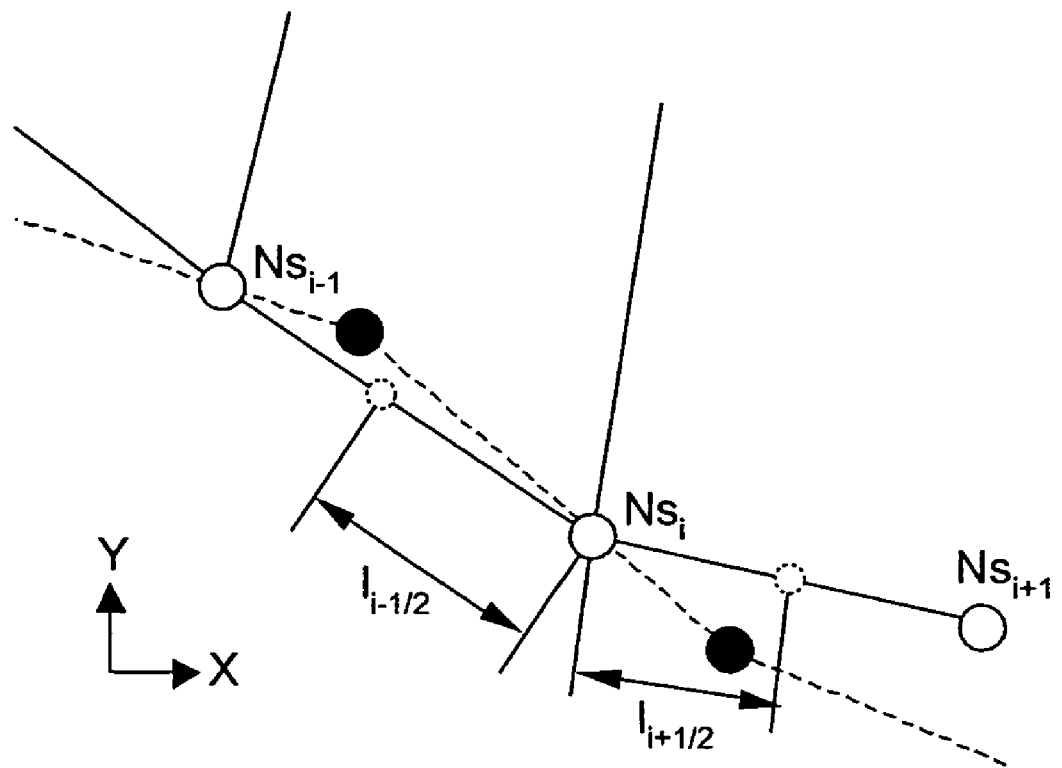
FIG. 25 is a diagram of the length covered by the node on the surface of the structure model in contact with the surface of the irregular surface model.

The contact-state evaluating unit 54 calculates the length or the area to be covered by a node on the surface of the structure model 11 (step S204). The procedures of this process are explained below. FIG. 24 is a flowchart of procedures for obtaining a length covered by a node on the surface of the structure model in contact with the surface of the irregular surface model. FIG. 25 is a diagram for explaining the length covered by the node on the surface of the structure model in contact with the surface of the irregular surface model.

In order to calculate the length covered by a node on the surface of the structure model 11, the contact-state evaluating unit 54 sets the number of node counts i of the structure model 11 to i=0 (step S501). Then, the contact-state evaluating unit 54 sets the number of node counts i to i=i+1(step S502). In this stage, because i=0 is set at step S501, the number of node counts i at step S502 becomes 1.

Here, the node $Ns_i$ on the surface of the structure model 11 that is in contact with the surface of the irregular surface model 10 is referred to. The contact-state evaluating unit 54 determines whether a node $Ns_{i-1}$ on the surface of the structure model 11 is in contact with the surface of the irregular surface model 10, from the data for the nodes on the surface of the structure model 11 obtained through determination at step S203 (step S503). If the node $Ns_{i-1}$ is in contact with the surface of the irregular surface model 10 (step S503; Yes), the contact-state evaluating unit 54 determines whether the node $Ns_{i+1}$ on the surface of the structure model 11 is in contact with the surface of the irregular surface model 10 (step S504).

If the node $Ns_{i+1}$ is in contact with the surface of the irregular surface model 10 (step S504; Yes), both of the nodes adjacent to the node $Ns_i$ are in contact with the surface of the irregular surface model 10. In this case, a sum of a distance $l_{i-1}$/2 and a distance $l_{i+1}$/2, namely, $(l_{i-1}+l_{i+1})$/2 is set as a contact length of the node $Ns_i$, where the distance $l_{i-1}$ is a distance between the node $Ns_i$ and the node $Ns_{i-1}$, and the distance $l_{i+1}$ is a distance between the node $Ns_i$ and the node $Ns_{i+1}$. The contact-state evaluating unit 54 calculates a length covered by the node $Ns_i$ (step S505), and stores data for the length in the storage unit 50m. The contact-state evaluating unit 54 calculates respective lengths covered by all nodes on the surface of the structure model 11 on the opposite side to the irregular surface model 10 (step S509; Yes).

If the node $Ns_{i-1}$ on the surface of the structure model 11 is not in contact with the surface of the irregular surface model 10 (step S503; No), the contact-state evaluating unit 54 determines whether the node $Ns_{i+1}$ on the surface of the structure model 11 is in contact with the surface of the irregular surface model 10 (step S506). If the node $Ns_{i+1}$ is not in contact with the surface of the irregular surface model 10 (step S506; No), both of the nodes adjacent to the node $Ns_i$ do not contact the surface of the irregular surface model 10. In this case, the length covered by the node $Ns_i$ is set to 0. The contact-state evaluating unit 54 stores this data in the storage unit 50m, and calculates respective lengths covered by all nodes on the surface of the structure model 11 on the opposite side to the irregular surface model 10 (step S509; Yes).

If the node $Ns_{i+1}$ on the surface of the structure model 11 is in contact with the surface of the irregular surface model 10

(step S506; Yes), only one node ($Ns_{i+1}$) of the nodes adjacent to the node $Ns_i$ is in contact with the surface of the irregular surface model 10. In this case, the distance $l_{i+1}/2$ is the length covered by the node $Ns_i$ (see FIG. 25). The contact-state evaluating unit 54 calculates the length covered by the node $Ns_i$ (step S507), and stores this data in the storage unit 50m. The contact-state evaluating unit 54 calculates respective lengths covered by all nodes on the surface of the structure model 11 on the opposite side to the irregular surface model 10 (step S509; Yes).

If the node $Ns_{i+1}$ on the surface of the structure model 11 is not in contact with the surface of the irregular surface model 10 (step S504; No), only one node ($Ns_{i-1}$) of the nodes adjacent to the node $Ns_i$ is in contact with the surface of the irregular surface model 10. In this case, the distance $l_{i-1}/2$ is the length covered by the node $Ns_i$ (see FIG. 25). The contact-state evaluating unit 54 calculates the length covered by the node $Ns_i$ (step S508), and stores the data in the storage unit 50m. The contact-state evaluating unit 54 calculates respective lengths covered by all nodes on the surface of the structure model 11 on the opposite side to the irregular surface model 10 (step S509; Yes).

According to the procedures, the length or the real contact length covered by each node on the surface of the structure model 11 on the opposite side to the irregular surface model 10 can be obtained (step S204). By summing the real contact lengths of the nodes (step S205), the whole real contact length between the irregular surface model 10 and the structure model 11 can be obtained. A contact pressure and an amount of wear acting on the nodes on the surface of the structure model 11 can be calculated based on the real contact lengths of the nodes on the surface of the structure model 11 obtained through the procedures. The contact pressure between the irregular surface model 10 and the structure model 11 can also be calculated from the whole real contact length obtained from the real contact lengths of the nodes through the procedures. Although the real contact length is obtained in the above explanation, to obtain a real contact area, a shared proportion of an area by the node $Ns_i$ may be obtained by referring to the node $Ns_i$ on the surface of the structure model 11 in contact with the surface of the irregular surface model 10 and using a relationship with nodes adjacent to the node $Ns_i$.

Figure 26:
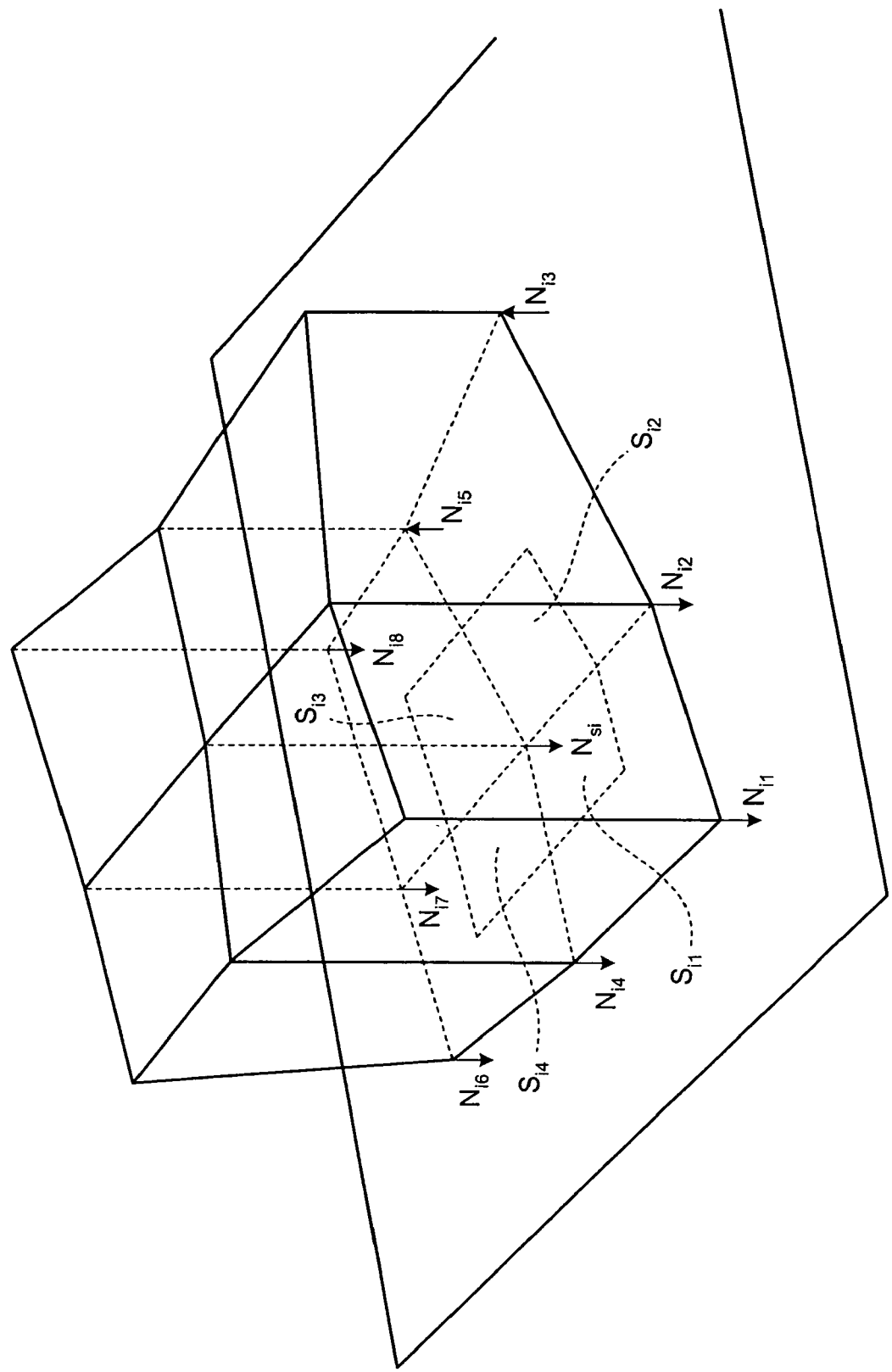
FIG. 26 is a diagram of an example of a three-dimensional structure and the irregular surface model.

The shared proportion of area is calculated based on a two-dimensional model, but in the present embodiment, it is not limited to the two-dimensional model. Therefore, the calculation can also be performed on a three-dimensional model. FIG. 26 is a diagram of an example of a three-dimensional structure and the irregular surface model. In a three-dimensional structure model, an area covered by the node $N_{si}$ is obtained in the following manner. First, it is determined whether the node $N_{si}$ is in contact with the irregular surface model. If it is not in contact with the irregular surface model, calculation for an area is not performed. If it is in contact with the irregular surface model, it is determined whether nodes around the node $Ns_i$ are in contact with the irregular surface model.

At this time, if both $N_{i2}$ and $N_{i4}$ as nodes adjacent to an element including the node $N_{si}$ are in contact with the irregular surface model, one-fourth of an element area including $N_{si}$, $N_{i2}$, and $N_{i4}$, i.e. $S_{i1}$ is regarded as an area covered by the node $N_{si}$. Areas $S_{i4}$ and $S_{i3}$ are obtained in the same manner as above, and an area $S=S_{i1}+S_{i4}+S_{i3}$ obtained by summing these values is regarded as a total area covered by the node $N_{si}$. In this case, a node $N_{i5}$ is not in contact with the irregular surface model, and therefore, an area $S_{i2}$ is not added to the area. As explained in the example, even if the calculation is performed on the three-dimensional model, a method of calculating ground contact area according to the present invention is applicable to the case, and this method is an analysis method excellent in scalability.

In the method according to the present embodiment, the analysis models for an irregular surface and a structure are created, and a real contact state of a contact area between the two is evaluated using the analysis method such as the finite element method. With these data, it is possible to obtain and evaluate the details of the real contact state on the surface of an irregular surface, i.e. an object having roughness. It is also possible to evaluate a real contact state on a surface having surface roughness in micrometer order, which cannot be obtained by the method disclosed in JP-A No. 2003-240681, by observation using a contact microscope conventionally used, or by ultrasonic evaluation for a contact surface. The real contact state on such the surface having surface roughness in micrometer order as above is extremely important to discuss a state of wear of the surface as a target for contact. Therefore, the method according to the present embodiment is useful for evaluation of the wear.

The real contact state on the surface having roughness is analyzed and evaluated by using the irregular surface model created based on the geometric shape data for the irregular surface of an object, which makes it possible to efficiently evaluate the real contact state on the rough surface. Furthermore, by using the irregular surface model created based on the geometric shape data for the irregular surface of an object, it is possible to understand and evaluate the contact state between a rough surface and a smooth surface or between surfaces having roughness. Although the evaluation for the contact state between the tire and the road surface is explained, the method according to the present embodiment can be used to evaluate a contact state between a seal surface and a seal material, a contact state between sliding members, or some other various contact states.

According to the present invention, it is possible to achieve at least one of those such as obtaining and evaluating details of a real contact state on a surface having roughness and efficiently evaluating a real contact state on a surface having roughness.

Although the invention has been described with respect to a specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. A method of evaluating contact characteristics of an object having a roughness, the method comprising:
    setting geometric shape data for the roughness;
    creating a roughness model and a structure model that comes in contact with the roughness, based on the geometric shape data set;
    making the roughness model and the structure model come in contact with each other;
    acquiring a physical amount occurring at least one of a contact region of the roughness model and a contact region of the structure model; and
    obtaining an evaluation value for evaluating a real contact state in the contact region between the roughness model and the structure model, from the physical amount acquired.

2. The method according to claim 1, wherein the structure model is divided into finite pieces of elements.

3. The method according to claim 2, wherein
    the finite pieces of elements include:

a first typical element included in a predetermined region from an outline of the roughness model; and a second typical element included in a region other than the predetermined region, and wherein a dimension of the first typical element is smaller than a dimension of the second typical element.

4. The method according to claim 3, wherein the dimension of the first typical element is in a range between 0.001 times the dimension of the second typical element and 0.1 times the dimension of the second typical element.

5. The method according to claim 2, wherein the roughness model is divided into finite pieces of elements, and a dimension of first minimum typical element from among the elements that form the structure model is equal to or less than a dimension of second minimum typical element from among the elements that form the roughness model.

6. The method according to claim 5, wherein the dimension of the first minimum typical element is in a range between 0.01 times the dimension of the second minimum typical element and 1.0 times the dimension of the second minimum typical element.

7. The method according to claim 2, wherein the structure model regenerates an element in a region that is affected by deformation due to the roughness model, according to the deformation.

8. The method according to claim 7, wherein a higher rigidity is 10 times or higher than a lower rigidity between a rigidity of the roughness model and a rigidity of the structure model.

9. The method according to claim 7, wherein a material of the structure model is an elastomer.

10. The method according to claim 1, wherein the geometric shape data for the roughness set is function-approximated over a whole region or in a part of the roughness of the roughness model.

11. The method according to claim 1, wherein the roughness model has a roughness that is formed by combining arbitrary geometric shapes.

12. A computer-readable recording medium that stores a computer program for evaluating contact characteristics of an object having a roughness, wherein the computer program causes a computer to execute setting geometric shape data for the roughness;

creating a roughness model and a structure model that comes in contact with the roughness, based on the geometric shape data set;

making the roughness model and the structure model come in contact with each other;

acquiring a physical amount occurring at least one of a contact region of the roughness model and a contact region of the structure model; and obtaining an evaluation value for evaluating a real contact state in the contact region between the roughness model and the structure model, from the physical amount acquired.

* * * * *